(12) United States Patent
Bark et al.

(10) Patent No.: US 9,248,134 B1
(45) Date of Patent: Feb. 2, 2016

(54) FE(III) COMPLEX COMPOUNDS FOR THE TREATMENT AND PROPHYLAXIS OF IRON DEFICIENCY SYMPTOMS AND IRON DEFICIENCY ANEMIAS

(71) Applicant: Vifor (International) AG, St. Gallen (CH)

(72) Inventors: Thomas Bark, Zürich (CH); Wilm Buhr, Constance (DE); Susanna Burckhardt, Zürich (CH); Michael Burgert, Friedrichshafen (DE); Camillo Canclini, St. Gallen (CH); Franz Dürrenberger, Dornach (CH); Felix Funk, Winterhur (CH); Peter O. Geisser, St. Gallen (CH); Aris Kalogerakis, Winterthur (CH); Simona Mayer, Bühler (CH); Erik Philipp, Arbon (CH); Diana Sieber, Abtwil (CH); Jörg Schmitt, Gaienhofen (DE); Katrin Schwarz, St. Gallen (CH); Stefan Reim, Stadel Winterthur (CH)

(73) Assignee: Vifor (International) AG, St. Gallen (CH)

( * ) Notice: Subject to any disclaimer, the term of this patent is extended or adjusted under 35 U.S.C. 154(b) by 0 days.

(21) Appl. No.: 14/770,601

(22) PCT Filed: Mar. 27, 2014

(86) PCT No.: PCT/EP2014/056146
§ 371 (c)(1),
(2) Date: Aug. 26, 2015

(87) PCT Pub. No.: WO2014/154797
PCT Pub. Date: Oct. 2, 2014

(30) Foreign Application Priority Data

Mar. 28, 2013 (EP) .................................. 13161698

(51) Int. Cl.
*A61K 31/555* (2006.01)
*C07F 15/02* (2006.01)
*A61K 45/06* (2006.01)

(52) U.S. Cl.
CPC ............... *A61K 31/555* (2013.01); *A61K 45/06* (2013.01)

(58) Field of Classification Search
USPC .............................................. 514/188; 546/2
See application file for complete search history.

(56) References Cited

U.S. PATENT DOCUMENTS

2013/0109662 A1    5/2013    Bark et al.

FOREIGN PATENT DOCUMENTS

WO    2012/163938 A1    12/2012

OTHER PUBLICATIONS

Notification of Transmittal of Translation of the International Preliminary Report on Patentability for corresponding PCT/EP2014/056146 mailed Oct. 8, 2015, seven pages.
International Search Report for corresponding PCT/EP2014/056146 mailed May 8, 2014, two pages.

*Primary Examiner* — Charanjit Aulakh
(74) *Attorney, Agent, or Firm* — Rankin, Hill & Clark LLP

(57) ABSTRACT

The invention relates to iron(III) complex compounds and pharmaceutical compositions comprising them for the use as medicaments, in particular for the treatment and/or prophylaxis of iron deficiency symptoms and iron deficiency anemias.

15 Claims, No Drawings

FE(III) COMPLEX COMPOUNDS FOR THE TREATMENT AND PROPHYLAXIS OF IRON DEFICIENCY SYMPTOMS AND IRON DEFICIENCY ANEMIAS

INTRODUCTION

The invention relates to iron(III)-3-hydroxy-isonicotinamide complex compounds and pharmaceutical compositions comprising them for the use as medicaments, in particular for the treatment and/or prophylaxis of iron deficiency symptoms and iron deficiency anemias.

BACKGROUND

Iron is an essential trace element for almost all organisms and is relevant in particular with respect to growth and the formation of blood. The balance of the iron metabolism is in this case primarily regulated on the level of iron recovery from hemoglobin of ageing erythrocytes and the duodenal absorption of dietary iron. The released iron is taken up via the intestine, in particular via specific transport systems (DMT-1, ferroportin, transferrin, transferrin receptors), transferred into the circulation and thereby conveyed to the appropriate tissues and organs.

In the human body, the element iron is of great importance for oxygen transport, oxygen uptake, cell functions such as mitochondrial electron transport, and ultimately for the entire energy metabolism.

On average, the human body contains 4 to 5 g iron, with it being present in enzymes, in hemoglobin and myoglobin, as well as depot or reserve iron in the form of ferritin and hemosiderin.

Approximately half of this iron, about 2 g, is present as heme iron, bound in the hemoglobin of the erythrocytes. Since these erythrocytes have only a limited lifespan (75-150 days), new ones have to be formed constantly and old ones eliminated (over 2 million erythrocytes are being formed per second). This high regenerative capacity is achieved by macrophages phagocytizing the ageing erythrocytes, lysing them and thus recycling the iron thus obtained for the iron metabolism. The amount of iron of about 25 mg required daily for erythropoiesis is thus provided for the main part.

The daily iron requirement of an adult human is between 0.5 to 1.5 mg per day, infants and women during pregnancy require 2 to 5 mg of iron per day. The daily iron loss, e.g. by desquamation of skin and epithelial cells, is low; increased iron loss occurs, for example, during menstrual hemorrhage in women. Generally, blood loss can significantly reduce the iron level since about 1 mg iron is lost per 2 ml blood. In a healthy human adult, the normal daily loss of iron of about 1 mg is usually replaced via the daily food intake. The iron level is regulated by absorption, with the absorption rate of the iron present in food being between 6 and 12%; in the case of iron deficiency, the absorption rate is up to 25%. The absorption rate is regulated by the organism depending on the iron requirement and the size of the iron store. In the process, the human organism utilizes both divalent as well as trivalent iron ions. Usually, iron(III) compounds are dissolved in the stomach at a sufficiently acid pH value and thus made available for absorption. The absorption of the iron is carried out in the upper small intestine by mucosal cells. In the process, trivalent non-heme iron is first reduced in the intestinal cell membrane to Fe(II) for absorption, for example by ferric reductase (membrane-bound duodenal cytochrome b), so that it can then be transported into the intestinal cells by means of the transport protein DMT1 (divalent metal transporter 1). In contrast, heme iron enters the enterocytes through the cell membrane without any change. In the enterocytes, iron is either stored in ferritin as depot iron, or discharged into the blood by the transport protein ferroportin. Hepcidin plays a central role in this process because it is the most important regulating factor of iron uptake. The divalent iron transported into the blood by ferroportin is converted into trivalent iron by oxithees (ceruloplasmin, hephaestin), the trivalent iron then being transported to the relevant places in the organism by transferrin (see for example "Balancing acts: molecular control of mammalian iron metabolism". M. W. Hentze, *Cell* 117, 2004, 285-297.)

Mammalian organisms are unable to actively discharge iron. The iron metabolism is substantially controlled by hepcidin via the cellular release of iron from macrophages, hepatocytes and enterocytes.

In pathological cases, a reduced serum iron level leads to a reduced hemoglobin level, reduced erythrocyte production and thus to anemia.

External symptoms of anemias include fatigue, pallor as well as reduced capacity for concentration. The clinical symptoms of an anemia include low serum iron levels (hypoferremia), low hemoglobin levels, low hematocrit levels as well as a reduced number of erythrocytes, reduced reticulocytes and elevated levels of soluble transferrin receptors.

Iron deficiency symptoms or iron anemias are treated by supplying iron. In this case, iron substitution takes place either orally or by intravenous iron administration. Furthermore, in order to boost erythrocyte formation, erythropoietin and other erythropoiesis-stimulating substances can also be used in the treatment of anemias.

Anemia can often be traced back to malnutrition or low-iron diets or imbalanced nutritional habits low in iron. Moreover, anemias occur due to reduced or poor iron absorption, for example because of gastroectomies or diseases such as Crohn's disease. Moreover, iron deficiency can occur as a consequence of increased blood loss, such as because of an injury, strong menstrual bleeding or blood donation. Furthermore, an increased iron requirement in the growth phase of adolescents and children as well as in pregnant women is known. Since iron deficiency not only leads to a reduced erythrocyte formation, but thereby also to a poor oxygen supply of the organism, which can lead to the above-mentioned symptoms such as fatigue, pallor, reduced powers of concentration, and especially in adolescents, to long-term negative effects on cognitive development, a highly effective and well tolerated therapy is of particular interest.

Through using the Fe(III) complex compounds according to the invention, there is the possibility of treating iron deficiency symptoms and iron deficiency anemias effectively by oral application without having to accept the large potential for side effects of the classical preparations, the Fe(II) iron salts, such as $FeSO_4$, which is caused by oxidative stress. Poor compliance, which often is the reason for the deficient elimination of the iron deficiency condition, is thus avoided.

PRIOR ART

A multitude of iron complexes for the treatment of iron deficiency conditions is known from the prior art.

A very large proportion of these complex compounds consists of polymer structures. Most of these complex compounds are iron-polysaccharide complex compounds (WO20081455586, WO2007062546, WO20040437865, US2003236224, EP150085). It is precisely from this area that there are medicaments available on the market (such as Maltofer, Venofer, Ferinject, Dexferrum, Ferumoxytol).

Another large portion of the group of the polymer complex compounds is comprised of the iron-peptide complex compounds (CN101481404, EP939083, JP02083400).

There are also Fe complex compounds described in the literature that are structurally derived from macromolecules such as hemoglobin, chlorophyll, curcumin and heparin (US474670, CN1687089, Biometals, 2009, 22, 701-710).

Moreover, low-molecular Fe complex compounds are also described in the literature. A large number of these Fe complex compounds comprises carboxylic acid and amino acids as ligands. In this case, the focus is on aspartate (US2009035385) and citrate (EP308362) as ligands. Fe complex compounds containing derivatized phenylalanine groups as ligands are also described in this context (ES2044777).

Further, Fe-complex compounds are described in the literature, which are built from monomeric sugar units or of a combination of monomeric and polymeric units (FR19671016).

Hydroxypyrone and hydroxypyridone Fe complex compounds are also described in the literature (EP159194, EP138420, EP107458, EP0120670). The corresponding 5-ring systems, the hydroxyfuranone Fe complex compounds, are also described in analogy thereto (WO2006037449). However, in particular the hydroxypyridone Fe complex compounds exhibit a comparably low water solubility, which makes them less suitable for the oral application. Further, the hydroxypyridone Fe complex compounds exhibit a comparably low iron utilization.

In addition, also Fe complex compounds with pyrimidine-2-ol-1-oxide ligands are described in the literature that should be used for the treatment of iron deficiency anemia (WO2012130882). The WO2012163938 describes iron (III)-2,4-dioxo-1-carbonyl complex compounds with ligands of the formula (I):

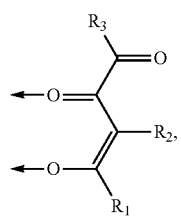

(I)

which shall also be used for the treatment of iron deficiency anemia. It becomes apparent, that by such ligand structure the ligands according to the general formula (I) of the present application

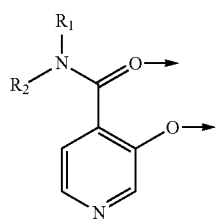

(I)

are not realized, still not in a case wherein the substituents indicated with $R_1$ and $R_2$ together would form a suitable heterocyclic aromatic ring. The remaining carbonyl residue ($R_3$—C(=O)—) is clearly different from the amide group, which is mandatorily present in the corresponding position in the present application.

Furthermore, Fe complexes with β-keto amide ligands are described in the literature, their use being proposed for the treatment of iron deficiency conditions. WO2011117225 discloses iron complex compounds, which are formed from β-keto amide ligands

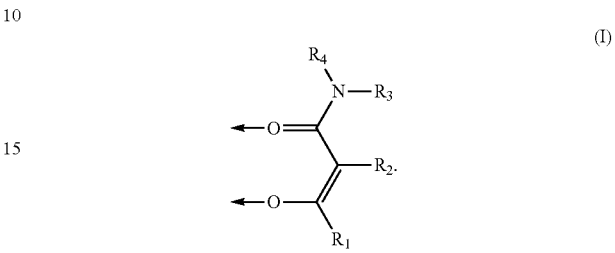

(I)

Regarding the meaning of the substituents $R_1$ and $R_2$ defined therein it is mentioned, that those together with the carbon atoms to which they are bonded may form an optionally substituted 5- or 6-membered ring, which may optionally contain one or more heteroatoms. However, no ring formation in the form of aromatic heterocyclic rings is mentioned. As concrete examples for ligands having such ring formation via $R_1$ and $R_2$ WO2011117225 shows

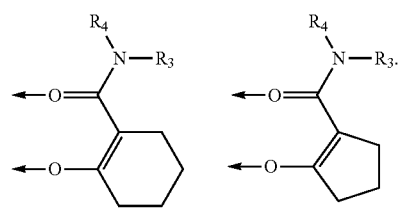

The only concretely disclosed iron(III) complex example compound exhibiting such ring formation via the substituents $R_1$ and $R_2$ is shown in Example 66 with a tris-(N, N-di methyl-2-oxocyclopentane:

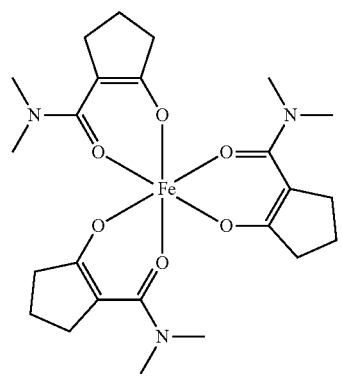

Heterocyclic aromatic ligands such as in particular iso nicotinamide ligands or iron(III) complexes formed thereof are not mentioned in WO2011117225. The cyclopentane or cyclohexane carboxamide iron(III) complexes shown therein exhibit, however, a very low stability which makes them nearly not applicable in pharmaceutical compositions and thus renders them unsuitable for medical applications.

Iron salts (e.g. iron(II) sulfate, iron(II) fumarate, iron(III) chloride, iron(II) aspartate, iron(II) succinate) are another important constituent for the treatment of iron deficiency symptoms and iron deficiency anemias.

These iron salts are very problematic in that, in part, they are highly incompatible (up to 50%) in the form of nausea, vomiting, diarrhea and also obstipation and cramps. Moreover, free iron(II) ions which catalyze the formation (inter alia Fenton reaction) of reactive oxygen species (ROS) occur during the use of these iron(II) salts. These ROS cause damage to DNA, lipids, proteins and carbohydrates which has far-reaching effects in cells, tissue and organs. This complex of problems is known and, in the literature, is largely considered the cause for the high incompatibility and referred to as oxidative stress.

OBJECT

The object of the present invention lay in developing new therapeutically effective compounds with good activity, iron utilization, complex stability and solubility, respectively, particularly good stability and good solubility in the pH of neutral aqueous media, that can be used for an effective therapy for the oral treatment of iron deficiency symptoms and iron deficiency anemias. Particularly a good stability and a good solubility is very important for an effective oral iron therapy.

Further, these iron complexes were supposed to exhibit significantly fewer side effects or a lower toxicity, particularly in comparison to the classically used Fe(II) salts. Furthermore, these iron complexes, in contrast to the known polymeric iron complex compounds, were supposed to have a defined structure (stoichiometry) and to be preparable by simple synthesis processes. This goal was achieved by the development of novel Fe(III) complex compounds.

Furthermore, the novel iron complexes were supposed to be designed such that they are taken up into the intestinal cells directly via the membrane in order thus to release their complex-bound iron directly to the ferritin or the transferrin or to reach the bloodstream directly as an intact complex. Because of their properties, these new complexes are supposed to virtually not lead to the occurrence of high concentrations of free iron ions. For it is precisely the free iron ions that lead to the occurrence of ROS which are ultimately responsible for the side effects that occur.

In order to be able to meet these requirements, the inventors developed new Fe(III) complex compounds with a molecular weight that is not too large, medium lipophilicity, very good activity or iron utilization, respectively, high water solubility and an optimal pH-dependent complex stability.

In the development of the new complexes, the stability improvement particularly in neutral aqueous media should not be achieved at the expense of solubility, since for oral use the solubility is a very important criterion. This combined goal is achieved by the Fe complexes of the invention. They show a good stability in aqueous medium at neutral pH, and at the same time have a very good solubility in water. Thus the iron complex compounds of the invention allow to achieve a much faster treatment success.

DESCRIPTION OF THE INVENTION

The inventors surprisingly found that novel Fe(III) complex compounds with 3-hydroxy-isonicotinamide ligands were particularly suitable for the above-described requirements.

The iron(III)-3-hydroxy-isonicotinamide complex compounds of the present invention may interchangeably also be designated "iron(III)-3-hydroxy-pyridin-4-carboxamide complex (compound)" and respectively the 3-hydroxy-isonicotinamide ligands of the present invention may interchangeably be designated as "3-hydroxy-N,N-dimethyl-pyridine-4-carboxamide" or "3-hydroxypyridine-4-carboxamide" or as the respective "-ligand".

It was possible to demonstrate that these Fe complex compounds exhibited a high iron uptake, whereby a quick therapeutic success in the treatment of iron deficiency anemia could be achieved. Especially in comparison to iron salts, the complex compounds according to the invention exhibit a faster and higher utilization. Furthermore, these new systems have significantly reduced side effects than the classically used iron salts since there is no noteworthy occurrence of free iron irons in this case. The complex compounds according to the invention exhibit almost no oxidative stress since there is no formation of free radicals. Thus, significantly fewer side effects occur in the case of these complex compounds than in the case of the Fe salts known from the prior art. The complex compounds exhibit good stability at acidic as well as at neutral pH value ranges, which is particularly advantageous for oral applications. The complex compounds can be prepared well and are optimally suitable for the formulation of medicaments, in particular for oral administration.

Thus, the subject matter of the invention are iron(III)-3-hydroxy-isonicotinamide complex compounds or their salts, particularly pharmaceutically acceptable salts for use as medicaments. The subject matter of the invention are thus also iron(III)-3-hydroxy-isonicotinamide complex compounds or their pharmaceutically acceptable salts for use in a method for therapeutic treatment of the human or animal body, respectively.

A further subject matter of the present invention are the iron(III)-3-hydroxy-isonicotinarnide complex compounds as defined herein per se (irrespective of a specific medical use).

The iron(III)-3-hydroxy-isonicotinamide complex compounds as used in accordance with the present invention particularly include such compounds which comprise the following structural element:

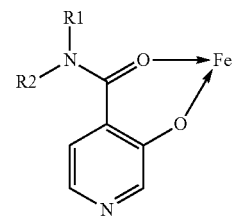

THE TERMS

"3-hydroxy-isonicotinamide",
"3-hydroxy-isonicotinamide compounds" or
"3-hydroxy-isonicotinamide ligands", such as interchangeably
"3-hydroxy-N,N-dimethyl-pyridine-4-carboxamide"
"3-hydroxy-N,N-dimethyl-pyridine-4-carboxamide compounds" or
"3-hydroxy-N,N-dimethyl-pyridine-4-carboxamide lidands", or interchangeably
"3-hydroxypyridine-4-carboxamide",
"3-hydroxypyridine-4-carboxamide compounds", or
"3-hydroxypyridine-4-carboxamide ligands"

according to the invention include the corresponding hydroxy starting compounds

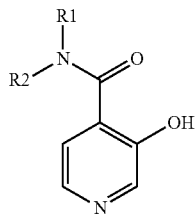

as well as the corresponding deprotonated ligands

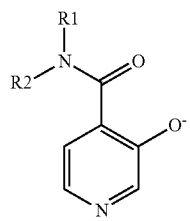

or

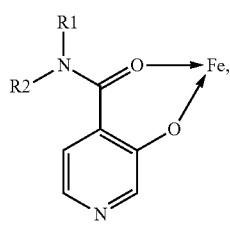

respectively which are present in the corresponding iron(III) complex compounds.

The ligand formally arises from the corresponding 3-hydroxy-isonicotinamide compounds by abstraction of a proton:

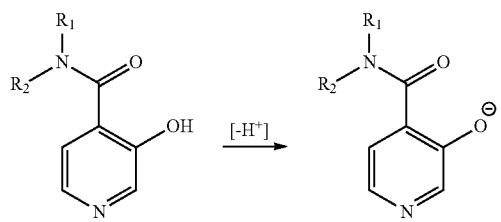

formally therefore carries a uninegative charge.

Accordingly, the aforementioned terms comprise in the sense of the present invention the respective base body:

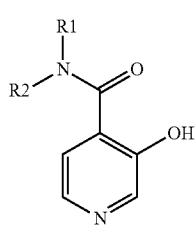

or the ligand compound resulting from deprotonating the underlying hydroxy compound

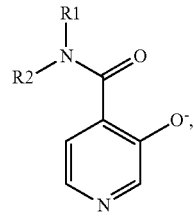

respectively.

According to the present invention the aforementioned terms thus designate the class of the "3-hydroxy-isonicotinamide compounds" or the deprotonated ligands, respectively, in its entirety.

Formally, a (deprotonated) 3-hydroxy-isonicotinamide ligand used according to the present invention thus formally carries, as shown above, a negative charge. This means, that in the case of three ligands per iron atom, the iron atom formally has the oxidation state +3.

In the iron(III) 3-hydroxy-isonicotinamide complex compounds according to the invention, the coordination number of the iron atoms is generally six (6), with a coordinating atoms generally being arranged octahedrally. Accordingly, the iron(III) 3-hydroxy-isonicotinamide complex compounds are preferably present as mononuclear complexes having at least one (1) central iron ion and three (3) 3-hydroxy-isonicotinamide ligands.

The iron(III) 3-hydroxy-isonicotinamide complex compounds of the present invention are generally present in neutral form. However, salt like iron(III) 3-hydroxy-isonicotinamide complex compounds are also included, in which the complex has a positive charge, which is compensated, in particular, by pharmacologically compatible, substantially non-coordinating anions (such as, in particular, halogenides, such as chloride).

The iron(III) 3-hydroxy-isonicotinamide complex compounds according to the invention particularly include complex compounds, comprising at least one, preferably a bidentate 3-hydroxy-isonicotinamide ligand of the formula

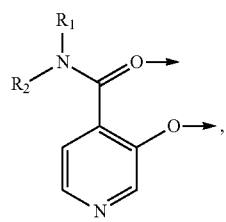

which can, as shown above, bond to one iron atom in the sense of bridging.

Iron(III) 3-hydroxy-isonicotinamide complex compounds are preferred which exclusively comprise preferably bidentate 3-hydroxy-isonicotinamide ligands which may be the same or different. Furthermore, iron(III) 3-hydroxy-isonicotinamide complex compounds are particularly preferred which exclusively comprise the same 3-hydroxy-isonicotinamide ligands and very particularly preferred are tris(3-hydroxy-isonicotinamide) iron(III) compounds.

In a particularly preferred embodiment the iron(III) complex compounds according to the present invention comprise three same or different, preferably same ligands of the formula (I):

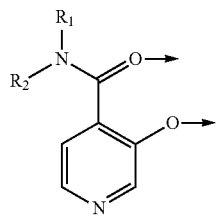

(I)

wherein
the arrows respectively represent a coordinate bond to one or different, preferably to one, iron atom;
$R_1$ and $R_2$ are the same or different and are in each case selected from the group consisting of:
hydrogen and
optionally substituted alkyl, or wherein
$R_1$ and $R_2$ together with the nitrogen atom to which they are bonded, form an optionally substituted 3- to 6-membered ring, which may optionally contain one further heteroatom, or pharmaceutically acceptable salts thereof.

Particularly preferred are iron(III) 3-hydroxy-isonicotinamide complex compounds containing at least one ligand of the formula (I):

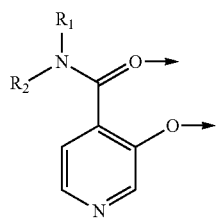

(I)

wherein
the arrows respectively represent a coordinate bond to one or different, preferably to one, iron atoms;
$R_1$ and $R_2$ are the same or different and are in each case selected from the group consisting of:
hydrogen and
optionally substituted alkyl, or wherein
$R_1$ and $R_2$ together with the nitrogen atom to which they are bonded, form an optionally substituted 5- to 6-membered ring, which may optionally contain one further heteroatom, or pharmaceutically acceptable salts thereof.

Further particularly preferred embodiments comprise iron (III)-3-hydroxy-isonicotinamide complex compounds, having at least one ligand of the formula (I):

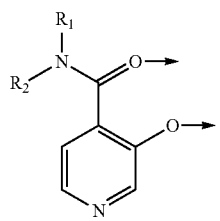

(I)

wherein
the arrows respectively represent a coordinate bond to one or different, preferably to one, iron atoms;
$R_1$ and $R_2$ are the same or different and are in each case selected from the group consisting of:
hydrogen and
optionally substituted alkyl, comprising in particular alkyl, wherein one or more methylene groups ($-CH_2-$) in the alkyl substituent can be replaced with $-O-$, and which may optionally be substituted with one or more alkoxy- and/or hydroxy groups; or wherein
$R_1$ and $R_2$ together with the nitrogen atom to which they are bonded, form an optionally substituted 5- to 6-membered ring, which may optionally contain one further heteroatom, or pharmaceutically acceptable salts thereof.

Even more preferred are embodiments comprising iron (III)-3-hydroxy-isonicotinamide complex compounds, having at least one ligand of the formula (I):

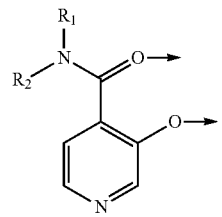

(I)

wherein
the arrows respectively represent a coordinate bond to one iron atom; $R_1$ and $R_2$ are the same or different and are in each case selected from the group consisting of:
hydrogen and
alkyl, comprising in particular alkyl, wherein one methylene group ($-CH_2-$) may be replaced with $-O-$, and which may optionally be substituted with one or more alkoxy groups; with the proviso that in the case of an alkyl group, wherein one methylene group ($-CH_2-$) is replaced with $-O-$, at least two methylene groups ($-CH_2-$) are present before such $-O-$ group and at least two methylene groups are present between such $-O-$ group and the $-O-$ group of the alkoxy substituent, corresponding to a structure according to $[(-CH_2-)_x-O-(CH_2-)_x-O-(CH_2)_yCH_3)]$,
wherein x in each case is an integer of 2 to 4 and y is an integer of 0 to 2;
or pharmaceutically acceptable salts thereof.

Therefrom very particularly preferred are iron(III)-3-hydroxy-isonicotinamide complex compounds having at least one ligand of the formula (I):

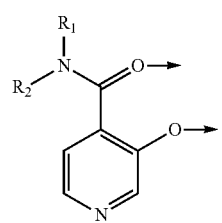

(I)

wherein
the arrows respectively represent a coordinate bond to one or different, preferably to one, iron atoms,
$R_1$ and $R_2$ are the same or different and are in each case selected from the group consisting of:
hydrogen,
methyl, ethyl, propyl, isopropyl, n-butyl, sek-butyl, isobutyl, methoxyethoxyethyl, ethoxyethoxyethyl, propoxyethoxyethyl,
methoxyethyl, ethoxyethyl, methoxypropyl and ethoxypropyl; or wherein
$R_1$ and $R_2$ together with the nitrogen atom to which they are bonded, form an optionally substituted heterocyclic 5- to 6-membered ring, which may optionally contain one further heteroatom, preferably an oxygen atom,
or pharmaceutically acceptable salts thereof.

Particularly preferred iron(III) complex compounds comprise at least one ligand of the formula (I):

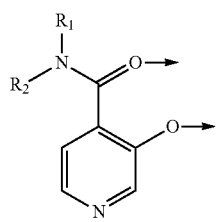

(I)

wherein
the arrows respectively represent a coordinate bond to one or different iron atoms, $R_1$ and $R_2$ are the same or different and are in each case selected from the group consisting of methyl, ethyl, propyl, n-butyl and alky being substituted with one methoxy group or with one ethoxy group; or wherein $R_1$ and $R_2$ together with the nitrogen atom to which they are bonded, form a heterocyclic 5- to 6-membered ring, which is selected from the group consisting of morpholinyl, piperidinyl and pyrrolidinyl,
or pharmaceutically acceptable salts thereof.

Particularly preferred are iron(III) complex compounds of the formula (II):

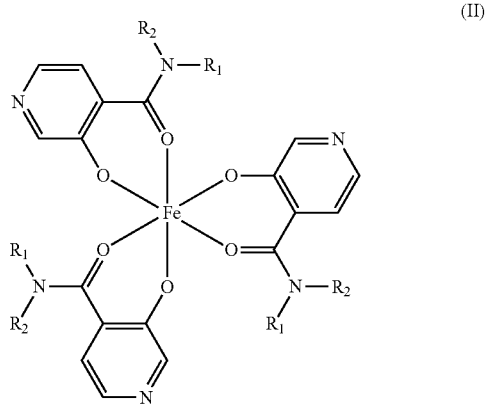

(II)

wherein $R_1$ and $R_2$ are as defined above.

Very particularly preferred are iron(III) complex compounds selected from the group:

Tris-(3-hydroxy-N,N-dimethylisonicotinamide) iron(III) complex

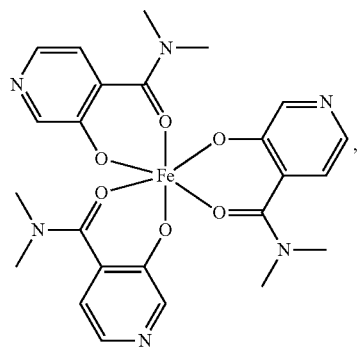

Tris-(3-hydroxy-isonicotinamide) iron(III) complex

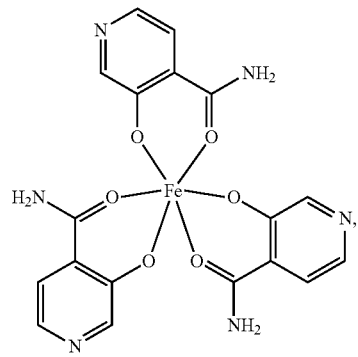

-continued
Tris-(3-hydroxy-N-methylisonicotinamide) iron(III) complex
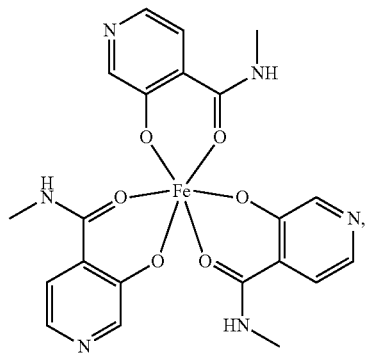
Tris-(3-hydroxy-N-ethylisonicotinamide) iron(III) complex
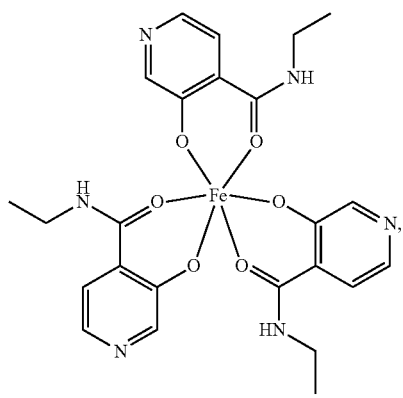
Tris-(3-hydroxy-N-propylisonicotinamide) iron(III) complex
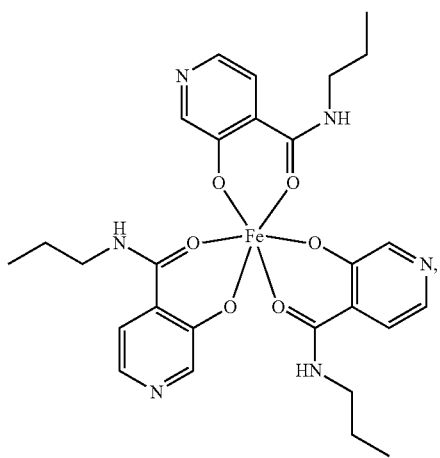

-continued
Tris-(N-butyl-3-hydroxyisonicotinamide) iron(III) complex
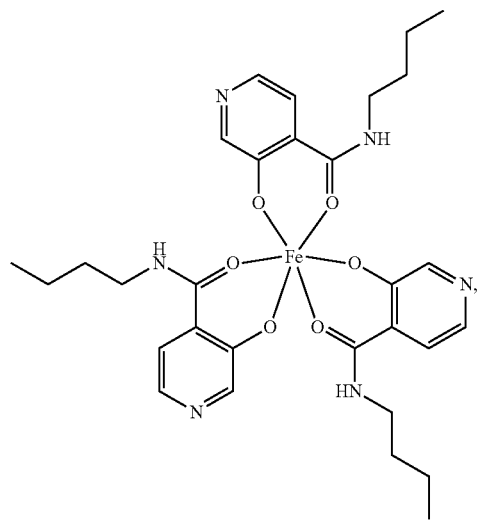
Tris-(3-hydroxy-N-(2-methoxyethyl)isonicotinamide) iron(III) complex
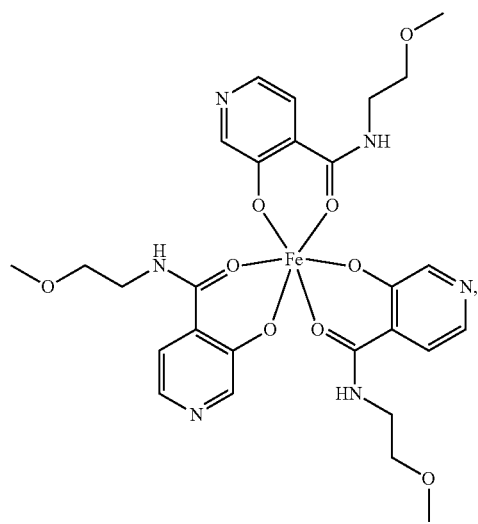
Tris-(3-hydroxy-N-(2-methoxyethyl)-N-methylisonicotinamide) iron(III) complex
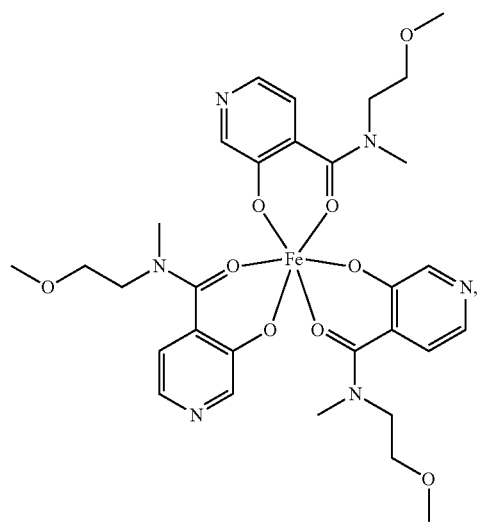

| | |
|---|---|
| Tris-(3-hydroxy-N,N-bis(2-methoxyethyl)isonicotinamide) iron(III) complex | 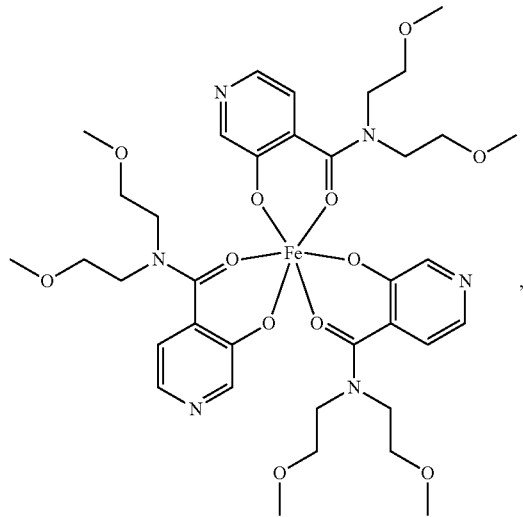 |
| Tris-(N,N-diethyl-3-hydroxyisonicotinamide) iron(III) complex | 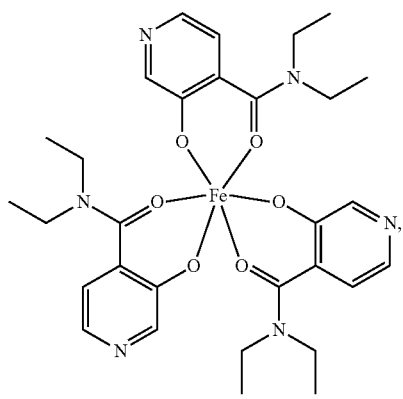 |
| Tris-((3-hydroxypyridine-4-yl)(morpholino)methanone) iron(III) complex | 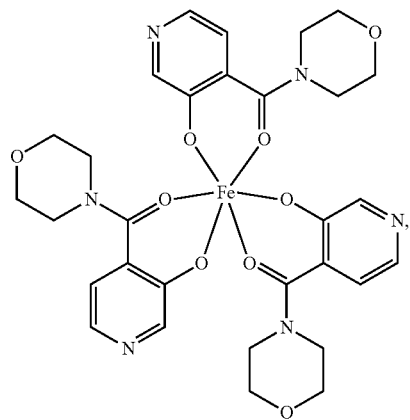 |

-continued

Tris-((3-hydroxypyridine-4-yl)(piperidine-1-yl)methanone) iron(III) complex

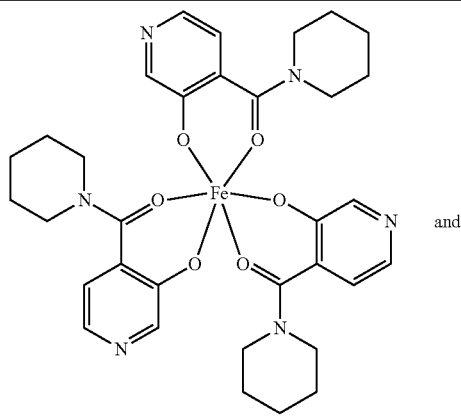

and

Tris-((3-hydroxypyridine-4-yl)(pyrrolidine-1-yl)methanone) iron(III) complex

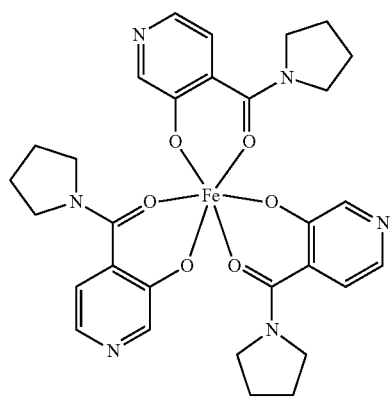

Preferably, the molecular weight of the iron(III) 3-hydroxy-isonicotinamide complex compounds is less than 1000 g/mol, more preferably less than 800 g/mol (each determined from the structural formula).

Within the overall context of the invention, optionally substituted alkyl, in particular for the substituents $R_1$ and $R_2$, preferably includes: straight-chained or branched alkyl with 1 to 9, preferably 1 to 6 carbon atoms, cycloalkyl with 3 to 6, preferably 5 or 6 carbon atoms, or alkyl with 1 to 4 carbon atoms, which is substituted with cycloalkyl, wherein these alkyl groups can be optionally substituted.

Said alkyl groups may optionally each carry preferably 1 to 3 substituents.

These substituents at the alkyl group are preferably selected from the group consisting of: hydroxy and optionally substituted alkoxy, in particular as defined below.

In the above defined alkyl groups, optionally one or two carbon atoms can furthermore be replaced by oxygen. This means, in particular, that one or two methylene groups (—$CH_2$—) can be replaced in the alkyl groups by —O—. Preferably in such embodiments one methylene group is replaced by —O—.

Examples of alkyl residues having 1 to 6 carbon atoms include: a methyl group, an ethyl group, a n-propyl group, an i-propyl group, a n-butyl group, an i-butyl group, a sec-butyl group, a t-butyl group, an n-pentyl group, an i-pentyl group, a sec-pentyl group, a t-pentyl group, a 2-methylbutyl group, a n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, etc. Those with 1 to 4 carbon atoms are preferred. Methyl, ethyl, n-propyl, and n-butyl are most preferred.

Cycloalkyl groups with 3 to 6 carbon atoms preferably include: a cyclopropyl group, a cyclobutyl group, a cyclopentyl group, and a cyclohexyl group. The cycloalkyl groups may optionally be substituted preferably with a substituent such as hydroxyl, alkyl such as in particular methyl and ethyl, or alkoxy such as in particular methoxy and ethoxy.

The definition of the optionally substituted alkyl groups also includes alkyl groups which are substituted by the above mentioned cycloalkyl groups, such as for example cyclopropylmethyl, cyclobutylmethyl, cyclopentylmethyl or cyclohexylmethyl.

Examples of an alkyl group substituted with hydroxy include the above-mentioned alkyl residues, which have 1 to 2 hydroxy residues, such as for example hydroxymethyl, 2-hydroxyethyl, 3-hydroxypropyl, 4-hydroxybutyl, etc.

Examples of an alkyl group substituted with alkoxy include the above-mentioned alkyl residues, which have 1 to 2 alkoxy residues as defined below, such as for example methoxymethyl, 2-methoxyethyl, 3-methoxypropyl, ethoxymethyl, 2-ethoxyethyl, 3-ethoxypropyl etc. Methoxyethyl, ethoxyethyl, methoxypropyl and ethoxypropyl are preferred, particularly preferred is 2-methoxyethyl.

It is further preferred that an alkyl residue, wherein one methylene group (—$CH_2$—) is replaced by —O—, is substituted with an alkoxy group, preferably methoxy, ethoxy or propoxy, with the proviso that at least two methylene groups (—$CH_2$—) are present before and after the resulting centrally placed —O— group, corresponding to [(—$CH_2$—)$_x$—O—(—$CH_2$—)$_x$—O—(—$CH_2$—)$_y$$CH_3$)], wherein x is an integer of 2 to 4 and y is an integer of 0 to 2. Respective examples include in particular methoxyethoxyethyl, ethoxyethoxyethyl, pro poxyethoxyethyl, methoxyethoxypropyl, ethoxyethoxypropyl, propoxyethoxypropyl, methoxyethoxybutyl, ethoxyethoxybutyl, propoxyethoxybutyl, methoxypropoxyethyl, ethoxypropoxyethyl, propoxypropoxyethyl, methoxypropoxypropyl, ethoxypropoxypropyl, propoxypropoxypropyl, methoxypropoxybutyl, ethoxypropoxybutyl, propoxypropoxybutyl, methoxybutoxyethyl, ethoxybutoxyethyl, propoxybutoxyethyl, methoxybutoxypropyl, ethoxybutoxypropyl, propoxybutoxypropyl, methoxybutoxybutyl, ethoxybutoxybutyl, propoxybutoxybutyl; preferred are methoxyethoxyethyl, ethoxyethoxyethyl and propoxyethoxyethyl.

Optionally substituted alkoxy (RO—) is formally derived from the above mentioned optionally substituted alkyl residues by adding an oxygen atom and includes in context with the present invention, for example, linear or branched alkoxy groups preferably with up to 4 carbon atoms, such as a methoxy group, an ethoxy group, a n-propyloxy group, and an i-propyloxy group, etc.

The alkoxy groups may optionally be substituted, such as with the above possible substituents for alkyl, in particular with 1 to 3, preferably 1 substituents.

Methoxy, ethoxy, and n-propoxy are preferred for alkoxy, particularly preferred is methoxy and ethoxy, even more preferred is methoxy.

Within the overall context of the invention the substituents $R_1$ and $R_2$ may together with the nitrogen atom to which they are bonded, form an optionally substituted 3- to 6-membered ring, in particular an optionally substituted 5- to 6-membered ring, which may optionally contain one further heteroatom preferably an oxygen atom. Preferably, therein $R_1$ and $R_2$ together with the nitrogen atom to which they are bonded form an aliphatic ring. Examples in accordance with the invention include saturated 3- to 6-membered, preferably 5- to 6-membered, heterocyclic rings, which are bonden via the nitrogen atom, and which may optionally contain a further heteroatom such as in particular O or N, preferably O, such as for example aziridinyl (aziridine-1-yl), substituted aziridine-1-yl, azetidinyl (azetidine-1-yl), substituted azetidine-1-yl, pyrrolidinyl (pyrrolidine-1-yl), substituted pyrrolidine-1-yl, piperidinyl, such as piperidine-1-yl, substituted piperidine-1-yl, imidazolinyl (imidazoline-1-yl), substituted imidazoline-1-yl, piperazinyl (piperazine-1-yl), substituted piperazine-1-yl, morpholinyl, substituted morpholinyl. Preferably $R_1$ and $R_2$ together with the nitrogen atom to which they are bonded form a pyrrolidinyl, piperidinyl or morpholinyl residue.

The invention further relates to a method for the preparation of the iron(III) complex compounds according to the invention which comprises the reaction of a 3-hydroxy-isonicotinamide (III), corresponding to the protonated form of the ligand of the invention, with an iron(III) salt (IV).

3-Hydroxy-isonicotinamides include in particular those of the formula (III):

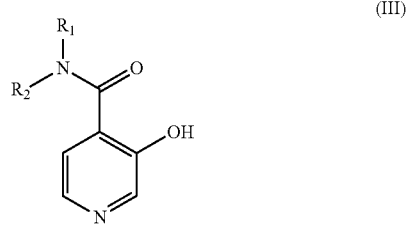

(III)

wherein $R_1$ and $R_2$ are as defined above.

Examples of suitable iron(III) salts include: iron(III) chloride, iron(III) acetate, iron(III) sulfate, iron(III) nitrate and iron(III) acetylacetonate, among which iron(III) chloride is preferred.

A preferred method is shown in the following scheme:

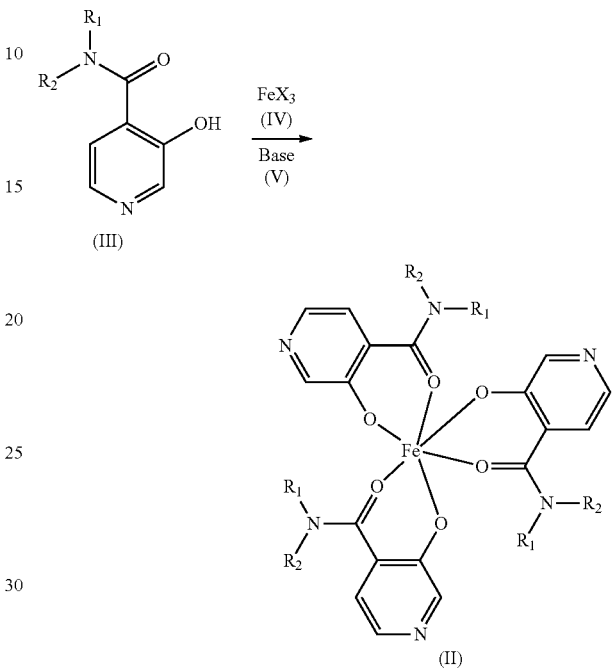

wherein $R_1$ and $R_2$ are as defined above, X is an anion such as halogenide, such as chloride, a carboxylate, such as acetate, sulphate, nitrate and acetylacetonate and base is a common organic or inorganic base.

In the method according to the invention, preferably 3 eq ligand (III), using suitable iron(III) salts (IV) (in this case Fe(III) chloride, Fe(III) acetate, Fe(III) sulphate and Fe(III) acetylacetonate are particularly suitable), are reacted under standard conditions to form the corresponding complexes of the general formula (II). In this case, the synthesis is carried out under the pH conditions optimal for complex formation. The optimum pH value is optionally set by adding a base (V), in this case, the use of triethylamine, sodium carbonate, sodium hydrogen carbonate, sodium hydrogen carbonate, sodium methanolate, sodium ethanolate, potassium carbonate, potassium hydrogen carbonate or potassium methanolate is particularly suitable.

The ligands (III) required for the preparation of the complexes are either commercially available or where prepared according to the following synthesis method. Therein the following synthesis route was followed.

The 3-hydroxy-isonicotinic acid ethyl ester (IV), required as the starting compound, was synthesized in analogy to Crum and Fuchsman (J. Heterocyclic Chem. 1966, 3, 252-256) and reacted with different amines of the general formula (VII) according to the general reaction equation to form the respective 3-hydroxy-isonicotinamides of the general formula (III). It is also possible to react 3-hydroxy-isonicotinic acid halogenides or activated 3-hydroxy-isonicotinic acid ester under standard reaction conditions which are well known to a person skilled in the art to form the desired compounds of the general formula (III).

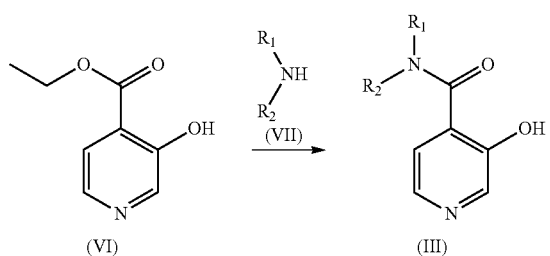

Pharmaceutically acceptable salts of the compounds according to the invention in which the iron(III) complex formally carries a positive charge include, for example, salts with suitable anions, such as carboxylates, sulfonates, sulfates, chlorides, bromides, iodides, phosphates, tartrates, methane sulfonates, hydroxyethane sulfonates, glycinates, maleates, propionates, fumarates, toluene sulfonates, benzene sulfonates, trifluoroacetates, naphthalenedisulfonates-1,5, salicylates, benzoates, lactates, salts of malic acid, salts of 3-hydroxy-2-naphthoic acid-2, citrates and acetates.

Pharmaceutically acceptable salts of the compounds according to the invention in which the iron(III) complex formally carries a negative charge include, for example, salts with suitable pharmaceutically acceptable bases, such as, for example, salts with alkaline or alkaline-earth hydroxides, such as NaOH, KOH, $Ca(OH)_2$, $Mg(OH)_2$ etc., amine compounds such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methylmorpholine, arginine, lysine, ethylenediamine, N-methylpiperidine, 2-amino-2-methyl-propanol-(1), 2-amino-2-methyl-propandiol-(1,3), 2-amino-2-hydroxyl-methyl-propandiol-(1,3) (TRIS) etc.

The water-solubility or the solubility in physiological saline solution and thus, optionally, also the efficacy of the compounds according to the invention can be significantly influenced by salt formation in general, specifically by the choice of the counterion.

Preferably, the compounds according to the invention constitute neutral complex compounds.

Advantageous Pharmacological Effects:

Surprisingly, the inventors found that the iron(III) 3-hydroxy-isonicotinamide complex compounds, which are the subject matter of the present invention and which are represented, in particular, by the general structural formula (II), are stable bioavailable iron complexes and suitable for use as a medicament for the treatment and prophylaxis of iron deficiency symptoms and iron deficiency anemias as well as the symptoms accompanying them.

The medicaments containing the compounds according to the invention are suitable for use in human and veterinary medicine.

The compounds according to the invention are thus also suitable for preparing a medicament for the treatment of patients suffering from symptoms of an iron deficiency anemia, such as, for example: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections or depressive moods.

The iron(III) complex compounds according to the invention are furthermore suitable for the treatment of iron deficiency anemia in pregnant women, latent iron deficiency anemia in children and adolescents, iron deficiency and iron deficiency anemia in children suffering from attention-deficit/hyperactivity disorder (ADHD) such as for the treatment of attention-deficit/hyperactivity disorder (ADHD) in children with or without iron deficiency and/or iron deficiency anemia, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CKD 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD).

Administration can take place over a period of several months until the iron status is improved, which is reflected, for example, by the hemoglobin level, transferrin saturation and the serum ferritin level of the patients, or until the desired improvement of the state of health affected by iron deficiency anemia.

The preparation according to the invention can be taken by children, adolescents and adults.

The applied compounds according to the invention can in this case be administered both orally as well as parentally. Oral administration is preferred.

The compounds according to the invention and the aforementioned combinations of the compounds according to the invention with other active substances or medicines can thus be used, in particular, for the preparation of medicaments for the treatment of iron deficiency anemia, such as iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), menstruation, injuries, iron deficiency anemia due to sprue, iron deficiency anemia due to reduced dietary iron uptake, in particular in selectively eating children and adolescents, immunodeficiency caused by iron deficiency anemia, brain function impairment caused by iron deficiency anemia, restless leg syndrome.

The application according to the invention leads to an improvement of the iron, hemoglobin, ferritin and transferrin levels, which, in particular in children and adolescents, but also in adults, is accompanied by an improvement in short-term memory tests (STM), long-term memory tests (LTM), Ravens' progressive matrices test, in the Wechsler adult intelligence scale (WAIS) and/or in the emotional coefficient (Baron EQ-i, YV test, youth version), or to an improvement of the neutrophile level, the antibody levels and/or lymphocyte function.

Furthermore, the present invention relates to pharmaceutical compositions comprising one or more of the compounds according to the invention, in particular according to the formula (II), as well as optionally one or more further pharmaceutically effective compounds, as well as optionally one or more pharmacologically acceptable carriers and/or auxiliary substances and/or solvents. The said pharmaceutical compositions contain, for example up to 99 weight-% or up to 90 weight-% or up to 80 weight-% or up to 70 weight-% of the compounds of the invention, the remainder being each formed by pharmacologically acceptable carriers and/or auxiliaries and/or solvents and/or optionally further pharmaceutically active compounds.

These are common pharmaceutical carriers, auxiliary substances or solvents. The above-mentioned pharmaceutical compositions are suitable, for example, for intravenous, intraperitoneal, intramuscular, intravaginal, intrabuccal, percutaneous, subcutaneous, mucocutaneous, oral, rectal, transdermal, topical, intradermal, intragasteral or intracutaneous application and are provided, for example, in the form of pills, tablets, enteric-coated tablets, film tablets, layer tablets, sustained release formulations for oral, subcutaneous or cutaneous administration (in particular as a plaster), depot formulations, dragees, suppositories, gels, salves, syrup, granulates, suppositories, emulsions, dispersions, microcapsules, microformulations, nanoformulations, liposomal formulations, capsules, enteric-coated capsules, powders, inhalation powders, microcrystalline formulations, inhalation sprays, epipastics, drops, nose drops, nose sprays, aerosols, ampoules, solutions, juices, suspensions, infusion solutions or injection solutions etc.

In a preferred embodiment of the invention the iron complex compounds are administered in the form of a tablet or capsule. These can for example be present as acid-resistant forms or with pH-dependent coatings.

Subject matter of the present invention are thus also compositions, containing the iron(III) complex compounds of the invention in combination with at least one further pharmaceutically active compounds. Examples of such pharmaceutically active compounds comprise in particular well known active substances or medicaments, which are applied together with agents for treating diseases associated with iron metabolism disorders and/or anemias (iron deficiency anemia), as well as such compounds which act on the iron metabolism and are thus preferably applied in the treatment of iron metabolism disorders. Examples of such agents for treating iron metabolism disorders and further diseases associated with iron metabolism disorders and/or anemias for combined application may for example comprise vitamin C and vitamin D and/or derivatives thereof.

Preferably the compounds of the invention as well as the pharmaceutical compositions, comprising such compounds, are applied orally, however, other forms such as parental, in particular intravenous application are also possible.

For this purpose, the compounds according to the invention are preferably provided in pharmaceutical compositions in the form of pills, tablets, enteric-coated tablets, film tablets, layer tablets, sustained release formulations for oral administration, depot formulations, dragees, granulates, emulsions, dispersions, microcapsules, microformulations, nanoformulations, liposomal formulations, capsules, enteric-coated capsules, powders, microcrystalline formulations, epipastics, drops, ampoules, solutions, suspensions, infusion solutions or injection solutions.

The compounds according to the invention can be administered in pharmaceutical compositions which may contain various organic or inorganic carrier and/or auxiliary materials as they are customarily used for pharmaceutical purposes, in particular for solid medicament formulations, such as, for example, excipients (such as saccharose, starch, mannitol, sorbitol, lactose, glucose, cellulose, talcum, calcium phosphate, calcium carbonate), binding agents (such as cellulose, methylcellulose, hydroxypropylcellulose, polypropyl pyrrolidone, gelatine, gum arabic, polyethylene glycol, saccharose, starch), disintegrating agents (such as starch, hydrolyzed starch, carboxymethylcellulose, calcium salt of carboxymethylcellulose, hydroxypropyl starch, sodium glycol starch, sodium bicarbonate, calcium phosphate, calcium citrate), lubricants (such as magnesium stearate, talcum, sodium laurylsulfate), a flavorant (such as citric acid, menthol, glycin, orange powder), preserving agents (such as sodium benzoate, sodium bisulfite, methylparabene, propylparabene), stabilizers (such as citric acid, sodium citrate, acetic acid and multicarboxylic acids from the titriplex series, such as, for example, diethylenetriaminepentaacetic acid (DTPA), suspending agents (such as methycellulose, polyvinyl pyrrolidone, aluminum stearate), dispersing agents, diluting agents (such as water, organic solvents), beeswax, cocoa butter, polyethylene glycol, white petrolatum, etc.

Liquid medicament formulations, such as solvents, suspensions and gels usually contain a liquid carrier, such as water and/or pharmaceutically acceptable organic solvents. Furthermore, such liquid formulations can also contain pH-adjusting agents, emulsifiers or dispersing agents, buffering agents, preserving agents, wetting agents, gelatinizing agents (for example methylcellulose), dyes and/or flavouring agents. The compositions may be isotonic, that is, they can have the same osmotic pressure as blood. The isotonicity of the composition can be adjusted by using sodium chloride and other pharmaceutically acceptable agents, such as, for example, dextrose, maltose, boric acid, sodium tartrate, propylene glycol and other inorganic or organic soluble substances. The viscosity of the liquid compositions can be adjusted by means of a pharmaceutically acceptable thickening agent, such as methylcellulose. Other suitable thickening agents include, for example, xanthan gum, carboxymethylcellulose, hydroxypropylcellulose, carbomer and the like. The preferred concentration of the thickening agent will depend on the agent selected. Pharmaceutically acceptable preserving agents can be used in order to increase the storage life of the liquid composition. Benzyl alcohol can be suitable, even though a plurality of preserving agents including, for example, parabene, thimerosal, chlorobutanol and benzalkonium chloride can also be used.

The active substance can be administered, for example, with a unit dose of 0.001 mg/kg to 500 mg/kg body weight, for example 1 to 4 times a day. However, the dose can be increased or reduced depending on the age, weight, condition of the patient, severity of the disease or type of administration.

EXAMPLES

The invention is illustrated in more detail by the following examples. The examples constitute only an exemplary illustration and it lies within the knowledge of a skilled person to extend the specific examples to further claimed compounds. The designation of the example names have been determined with the program ChemDraw Ultra Version 12.0.

Starting Compounds:

The starting compounds used in the examples were obtained as follows.

A. 3-Hydroxy-N,N-dimethylisonicotinamide

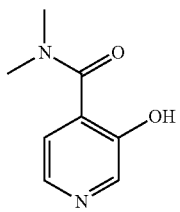

0.09 mol (15 g) 3-hydroxyisonicotinic acid ethyl ester (in analogy to J. D. Crum, C. H. Fuchsman, *J. Heterocyclic Chem.* 1966, 3, 252-256) and 0.9 mol dimethylamine (160 ml 5.6 M solution in ethanol) were heated in a pressure vessel to 120° C. for 5 h. Then the reaction mixture was evaporated until dryness and the crude product was recrystallized from 200 ml tetrahydrofuran and 100 ml ethanol. 10 g (67% yield) of the title compound were obtained.

IR (in substance, cm$^{-1}$): 1626, 1601, 1573, 1501, 1444, 1418, 1394, 1300, 1263, 1238, 1202, 1166, 1084, 1066, 964, 934, 838, 780, 741, 711, 645.

LC-MS (m/z): 167.5 (M+H).

CHN-elementary analysis: C, 58.22; H, 6.20; N, 16.72.

1H-NMR (DMSO-d$_6$, 400 MHz): δ [ppm]=10.29 (s, 1H), 8.22 (s, 1H), 8.06 (d, 1H), 7.11 (d, 1H), 2.95 (s, 3H), 2.77 (s, 3H).

B. 3-Hydroxyisonicotinamide

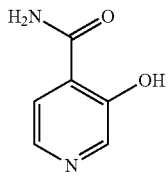

0.072 mol (12 g) 3-hydroxyisonicotinic acid ethyl ester and 0.72 mol ammonia (103 ml 7 M solution in methanol) were heated in a pressure vessel to 120° C. for 5 h. Then the reaction mixture was evaporated until dryness, suspended with 165 ml tetrahydrofuran and heated under reflux for 30 min. After cooling the product was filtered off and dried. 5 g (50% yield) of the title compound were obtained.

IR (in substance, cm$^{-1}$): 1699, 1665, 1638, 1597, 1561, 1498, 1440, 1418, 1349, 1310, 1250, 1227, 1197, 1096, 1063, 1027, 911, 788, 767, 672, 653, 623.

LC-MS (m/z): 139.4 (M+H).

CHN-elementary analysis: C, 50.92; H, 4.21; N, 19.16.

1H-NMR (DMSO-d$_6$, 400 MHz): δ [ppm]=8.52 (s, 1H), 8.37 (s, 1H), 8.21 (s, 1H), 8.18 (d, 1H), 7.80 (d, 1H).

C. 3-Hydroxy-N-methylisonicotinamide

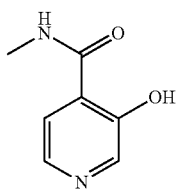

0.072 mol (12 g) 3-hydroxyisonicotinic acid ethyl ester and 0.25 mol dimethylamine (31 ml 33% solution in ethanol) were heated in a pressure vessel to 120° C. for 3 h. Then the reaction mixture was evaporated until dryness. The crude product was recrystallized from 130 ml tert-butylmethylester and 120 ml ethanol and then purified by chromatography over silica with ethyl acetate/methanol 9/1 plus 1% acetic acid as eluent. 6 g (55% yield) of the title compound were obtained.

IR (in substance, cm$^{-1}$): 1646, 1539, 1428, 1405, 1360, 1184, 1060, 1019, 893, 859, 818, 785, 664.

LC-MS (m/z): 153.8 (M+H).

CHN-elementary analysis: C, 55.18; H, 5.46; N, 18.36.

1H-NMR (DMSO-d$_6$, 400 MHz): δ [ppm]=12.17 (s, 1H), 8.94 (breit, 1H), 8.34 (s, 1H), 8.15 (d, 1H), 7.69 (d, 1H), 2.85 (d, 3H).

D. 3-Hydroxy-N-ethylisonicotinamide

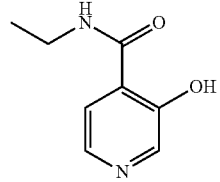

0.072 mol (12 g) 3-hydroxyisonicotinic acid ethyl ester and 0.22 mol ethylamine (108 ml 2 M solution in methanol) were heated in a pressure vessel to 100° C. for 2 h. Then the reaction mixture was evaporated until dryness and the crude product was recrystallized from 400 ml ethyl acetate and 20 ml ethanol. 7.8 g (65% yield) of the title compound were obtained.

IR (in substance, cm$^{-1}$): 1643, 1527, 1481, 1443, 1353, 1293, 1211, 1150, 1060, 843, 814, 783, 663.

CHN-elementary analysis: C, 57.68; H, 6.15; N, 16.81.

1H-NMR (DMSO-d$_6$, 400 MHz): δ [ppm]=12.21 (s, 1H), 8.97 (m, 1H), 8.34 (s, 1H), 8.15 (d, 1H), 7.72 (d, 1H), 3.35 (m, 2H), 1.16 (t, 3H).

E. 3-Hydroxy-N-propylisonicotinamide

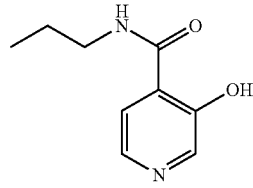

0.072 mol (12 g) 3-hydroxyisonicotinic acid ethyl ester and 0.3 mol n-propylamine (24.5 ml) were heated in a pressure vessel to 100° C. for 2 h. Then the reaction mixture was evaporated until dryness and the crude product was purified by chromatography over silica with ethyl acetate/methanol 4/1 as eluent. 6.4 g (49% yield) of the title compound were obtained.

IR (in substance, cm$^{-1}$): 1640, 1597, 1542, 1492, 1462, 1416, 1322, 1304, 1217, 1150, 1128, 1061, 979, 914, 815, 786, 735, 667.

LC-MS (m/z): 181.5 (M+H).

CHN-elementary analysis: C, 56.33; H, 6.57; N, 14.27.

1H-NMR (DMSO-d$_6$, 400 MHz): δ [ppm]=12.17 (breit, 1H), 8.96 (m, 1H), 8.33 (s, 1H), 8.14 (d, 1H), 7.72 (d, 1H), 3.28 (q, 2H), 1.56 (hextett, 2H), 0.90 (t, 3H).

F. N-Butyl-3-hydroxyisonicotinamide

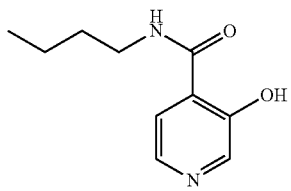

0.054 mol (9 g) 3-hydroxyisonicotinic acid ethyl ester and 0.27 mol n-butylamine (26.7 ml) were heated to 90° C. for 3 h. Then excessive n-butylamine was distilled under vacuum and the crude product was purified by chromatography over silica with ethyl acetate/methanol 4/1 as eluent. 7.7 g (74% yield) of the title compound were obtained.

IR (in substance, cm$^{-1}$): 1632, 1599, 1549, 1465, 1416, 1334, 1211, 1177, 1117, 1056, 951, 921, 878, 829, 788, 734, 701, 660, 599, 557.

LC-MS (m/z): 195.1 (M+H).

CHN-elementary analysis: C, 60.33; H, 7.76; N, 14.32.

1H-NMR (DMSO-d$_6$, 400 MHz): δ [ppm]=12.2 (breit, 1H), 8.92 (s, 1H), 8.30 (s, 1H), 8.12 (d, 1H), 7.70 (d, 1H), 3.29 (q, 2H), 1.52 (quintett, 2H), 1.31 (sextett, 2H), 0.88 (t, 3H).

G. 3-Hydroxy-N-(2-methoxyethyl)isonicotinamide

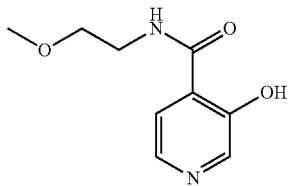

0.072 mol (12 g) 3-hydroxyisonicotinic acid ethyl ester and 0.36 mol (31.2 ml) 2-methoxyethylamine were heated under reflux for 3 h. Then excessive 2-methoxyethylamine was distilled under vacuum and the crude product was purified by chromatography over silica with ethyl acetate/methanol 9/1 as eluent. 9.3 g (66% yield) of the title compound were obtained.

IR (in substance, cm$^{-1}$): 1645, 1592, 1537, 1493, 1454, 1428, 1409, 1346, 1326, 1308, 1243, 1224, 1194, 1163, 1131, 1115, 1092, 1065, 1051, 1017, 908, 887, 818, 795, 671.

LC-MS (m/z): 197 (M+H).

CHN-elementary analysis: C, 54.91; H, 6.14; N, 14.26.

1H-NMR (DMSO-d$_6$, 400 MHz): δ [ppm]=12.08 (s, 1H), 8.99 (s, 1H), 8.34 (s, 1H), 8.15 (d, 1H), 7.75 (d, 1H), 3.50 (m, 4H), 3.29 (s, 3H).

H. 3-Hydroxy-N-(2-methoxyethyl)-N-methylisonicotinamide

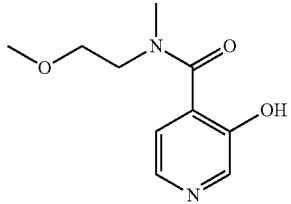

0.072 mol (12 g) 3-hydroxyisonicotinic acid ethyl ester and 0.223 mol (20.8 ml) N-(2-methoxyethyl)methylamine were heated under reflux for 3 h. Then excessive 2-methoxyethylamine was distilled under vacuum and the crude product was purified by chromatography over silica with ethyl acetate/methanol 9/1 as eluent. 14 g (92% yield) of the title compound were obtained.

IR (in substance, cm$^{-1}$): 1633, 1600, 1569, 1478, 1453, 1415, 1397, 1309, 1296, 1264, 1247, 1237, 1195, 1164, 1127, 1088, 1063, 976, 932, 895, 837, 793, 778, 742, 721, 643, 613.

LC-MS (m/z): 211.6 (M+H).

CHN-elementary analysis: C, 56.93; H, 6.70; N, 13.28.

1H-NMR (DMSO-d$_6$, 400 MHz): δ [ppm]=10.27 (s, 1H), 1.23/1.22 (s, 1H), 8.08/8.07 (d, 1H), 7.12/7.11 (d, 1H), 3.59/3.54 (t, 2H), 3.36/3.25 (t, 2H), 3.29/3.14 (s, 3H), 2.98/2.82 (s, 3H), (double set of signals in the ratio 53:47 due to E/Z-isomerie).

I. 3-Hydroxy-N,N-bis(2-methoxyethyl)isonicotinamide

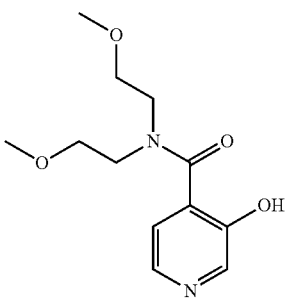

0.084 mol (14 g) 3-hydroxyisonicotinic acid ethyl ester and 0.108 mol (14.38 g) bis-(2-methoxyethyl)amine were heated to 110° C. for 6 h. Then the crude product was purified by chromatography over silica with ethyl acetate/methanol 5/1 as eluent. 6.19 g (30% yield) of the title compound were obtained.

IR (in substance, cm$^{-1}$): 1633, 1597, 1463, 1416, 1364, 1306, 1232, 1202, 1181, 1114, 1066, 1015, 828, 777, 744.

LC-MS (m/z): 255.5 (M+H).

CHN-elementary analysis: C, 54.14; H, 7.30; N, 10.49.

1H-NMR (DMSO-d$_6$, 400 MHz): δ [ppm]=10.25 (s, 1H), 8.21 (s, 1H), 8.07 (d, 1H), 7.10 (d, 1H), 3.61 (t, 2H), 3.52 (t, 2H), 3.34 (t, 2H), 3.29 (m, 5H), 3.12 (s, 3H).

J. N,N-Diethyl-3-hydroxyisonicotinamide

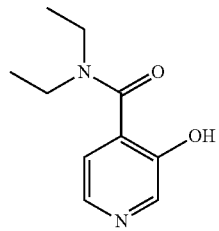

0.072 mol (12.4 g) 3-hydroxyisonicotinic acid ethyl ester and 0.49 mol diethylamine (51 ml) were stirred in a pressure vessel to 110° C. for 3 h. Then the reaction mixture was evaporated until dryness. The crude product was dissolved in 20 ml ethyl acetate, after addition of 20 ml diethylether it was stirred for 1 h and filtered, the filtration residue was dried. 11.3 g (80% yield) of the title compound were obtained.

IR (in substance, cm$^{-1}$): 1630, 1564, 1500, 1479, 1458, 1431, 1383, 1360, 1313, 1298, 1288, 1253, 1222, 1197, 1167, 1095, 1069, 945, 907, 881, 862, 832, 783, 737, 699, 636, 605.

LC-MS (m/z): 195.2 (M+H).

CHN-elementary analysis: C, 61.58; H, 7.15; N, 14.43.

1H-NMR (DMSO-d$_6$, 400 MHz): δ [ppm]=10.20 (s, 1H), 8.22 (s, 1H), 8.07 (d, 1H), 7.11 (d, 1H), 3.43 (q, 2H), 3.08 (q, 2H), 1.13 (t, 3H), 0.99 (t, 3H).

K. (3-Hydroxypyridine-4-yl)(morpholino)methanone

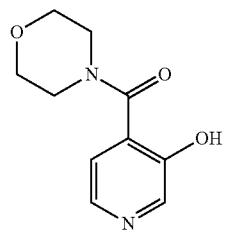

0.07 mol (12 g) 3-hydroxyisonicotinic acid ethyl ester and 0.288 mol morpholine (25 ml) were stirred for 4 h at 100° C. Then excessive morpholine was distilled under repeated addition of toluene and the crude product was recrystallized from 140 ml ethyl acetate and 130 ml ethanol. 11.5 g (79% yield) of the title compound were obtained.

IR (in substance, cm$^{-1}$): 1642, 1606, 1576, 1507, 1451, 1429, 1361, 1328, 1304, 1276, 1266, 1234, 1177, 1140, 1111, 1062, 1016, 907, 896, 858, 830, 773, 742, 712, 648, 623.

LC-MS (m/z): 209.7 (M+H).

CHN-elementary analysis: C, 57.69; H, 5.80; N, 13.47.

1H-NMR (DMSO-d$_6$, 400 MHz): δ [ppm]=10.35 (s, 1H), 8.23 (s, 1H), 8.09 (d, 1H), 7.17 (d, 1H), 3.62 (m, 4H), 3.53 (t, 2H), 3.16 (t, 2H).

L. (3-Hydroxypyridine-4-yl)(piperidine-1-yl)methanone

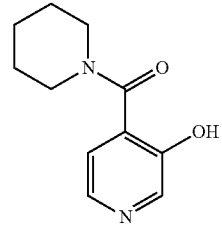

0.072 mol (12 g) 3-hydroxyisonicotinic acid ethyl ester and 0.39 mol piperidine (40 ml) were stirred for 3 h at 100° C. Then excessive piperidine was distilled under repeated addition of ethanol. The residue was suspended in 100 ml ethyl acetate, stirred for 1 h and precipitated product was filtered off. After drying 13 g (88% yield) of the title compound were obtained.

IR (in substance, cm$^{-1}$): 1631, 1606, 1573, 1505, 1427, 1363, 1351, 1303, 1280, 1252, 1232, 1184, 1126, 1109, 1063, 1029, 1002, 951, 931, 909, 885, 847, 822, 772, 742, 707, 639, 617.

LC-MS (m/z): 207.6 (M+H).

CHN-elementary analysis: C, 64.08; H, 6.862; N, 13.59.

1H-NMR (DMSO-d$_6$, 400 MHz): δ [ppm]=10.23 (s, 1H), 8.21 (s, 1H), 8.06 (d, 1H), 7.12 (d, 1H), 3.57 (m, 2H), 3.11 (m, 2H), 1.59 (m, 2H), 1.52 (m, 2H), 1.44 (m, 2H).

M. (3-Hydroxypyridine-4-yl)(pyrrolidine-1-yl)methanone

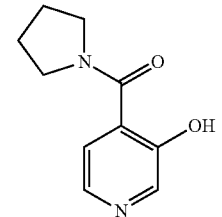

0.072 mol (12 g) 3-hydroxyisonicotinic acid ethyl ester and 0.48 mol pyrrolidine (40 ml) were heated under reflux for 3 h. Then excessive pyrrolidine was distilled under repeated addition of ethanol. The residue was suspended in 100 ml ethyl acetate, stirred for 1 h and the product was filtered off. After drying 8.1 g (42% yield) of the title compound were obtained.

IR (in substance, cm$^{-1}$): 1575, 1470, 1452, 1414, 1383, 1336, 1306, 1258, 1223, 1200, 1179, 1067, 856, 831, 796, 775, 735, 654.

LC-MS (m/z): 193.6 (M+H).

CHN-elementary analysis: C, 62.27; H, 6.57; N, 14.47.

1H-NMR (DMSO-d$_6$, 400 MHz): δ [ppm]=10.33 (s, 1H), 8.25 (s, 1H), 8.08 (d, 1H), 7.16 (d, 1H), 3.44 (d, 2H), 3.20 (d, 2H), 1.81 (m, 4H).

PREPARATION EXAMPLES

Example 1

Tris-(3-hydroxy-N,N-dimethylisonicotinamide) iron(III) complex:

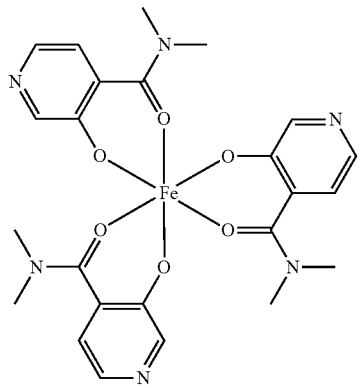

72 mmol (12 g) 3-hydroxy-N,N-dimethylisonicotinamide were provided in 250 ml ethanol and 72 mmol sodium methanolate (30% solution in methanol) were added. 24 mmol (3.89 g) FeCl$_3$ (anhydrous) were dissolved in 20 ml ethanol, added dropwise and stirred for 2 h. The reaction mixture was filtered off, the filtrate was evaporated at a rotary evaporator and the residue was dried. 13.6 g (96% Fe-yield) of the title compound were obtained.

IR (in substance, cm$^{-1}$): 1574, 1525, 1473, 1394, 1308, 1273, 1236, 1206, 1161, 1059, 928, 867, 850, 826, 790, 732, 711, 652, 615.

CHN-elementary analysis: C, 51.11; H, 5.44; N, 14.37.

Fe-content: 9.47% [m/m]

2. Tris-(3-Hydroxyisonicotinamide) iron(III) complex

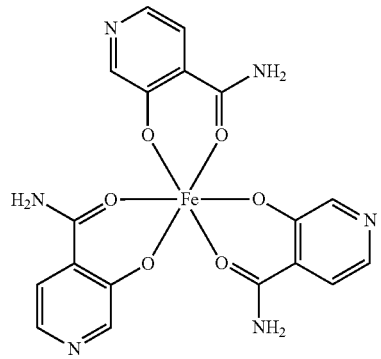

9 mmol (1.37 g) 3-hydroxyisonicotinamide were dissolved in 60 ml methanol under slight heating and 3 mmol (0.49 g) FeCl$_3$ (anhydrous) as well as 9 mmol sodium methanolate (1.67 ml of a 30% solution in methanol) were added. It was stirred for 0.5 h, the reaction mixture was evaporated to the half and filtered. The filtrate was evaporated to dryness at a rotary evaporator and the residue was dried at 50° C. in a vacuum drying oven. 1.84 g (96% Fe-yield) of the title compound were obtained.

IR (in substance, cm$^{-1}$): 1644, 1596, 1561, 1477, 1445, 1395, 1320, 1221, 1102, 1065, 1012, 904, 877, 827, 787, 761, 651, 618.

CHN-elementary analysis: C, 35.75; H, 2.92; N, 13.53.
Fe-content: 8.71% [m/m]
chloride-content: 12.1% [m/m]

3. Tris-(3-Hydroxy-N-methylisonicotinamide) iron(III) complex

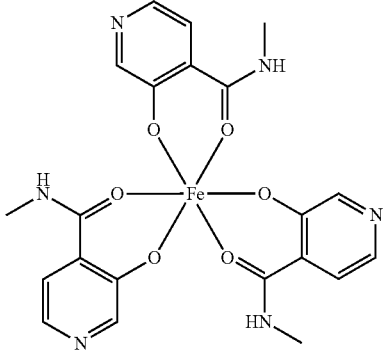

9 mmol (1.37 g) 3-hydroxy-N-methylisonicotinamide were dissolved in 20 ml ethanol and 3 mmol sodium methanolate (2.06 ml 25% solution in methanol) were added. 3 mmol (0.487 g) FeCl$_3$ (anhydrous) dissolved in 10 ml ethanol were added dropwise and stirred for 2 h. The reaction mixture was filtered, the filtrate was evaporated at a rotary evaporator and the residue was dried at 50° C. in a vacuum drying oven. 1.61 g (95% Fe-yield) of the title compound were obtained.

IR (in substance, cm$^{-1}$): 1590, 1548, 1474, 1406, 1319, 1217, 1155, 1125, 1067, 966, 904, 881, 832, 784, 665.

CHN-elementary analysis: C, 47.21; H, 4.73; N, 15.38.
Fe-content: 9.91% [m/m]
chloride-content: 0.64% [m/m]

4. Tris-(3-Hydroxy-N-ethylisonicotinamide) iron(III) complex

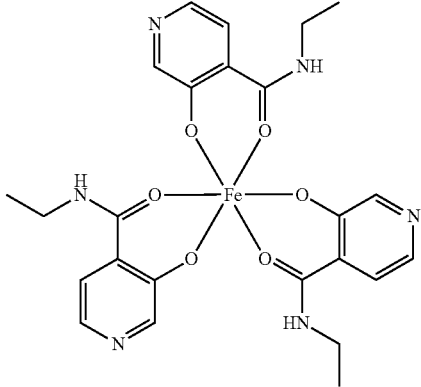

9 mmol (1.5 g) 3-hydroxy-N-ethylisonicotinamide were provided in 20 ml ethanol and 9 mmol sodium methanolate (2.06 ml 25% solution in methanol) were added. 3 mmol (0.49 g) FeCl$_3$ (anhydrous) dissolved in 10 ml ethanol were added dropwise and stirred for 2 h. The reaction mixture was filtered, the filtrate was evaporated at a rotary evaporator and the residue was dried at 50° C. in a vacuum drying oven. 1.71 g (96% Fe-yield) of the title compound were obtained.

IR (in substance, cm$^{-1}$): 1583, 1546, 1473, 1403, 1321, 1264, 1216, 1146, 1128, 1070, 1037, 898, 838, 784, 698, 665.

CHN-elementary analysis: C, 48.07; H, 4.99; N, 13.97.
Fe-content: 9.43% [m/m]
chloride-content: 2.92% [m/m]

5. Tris-(3-Hydroxy-N-propylisonicotinamide) iron(III) complex

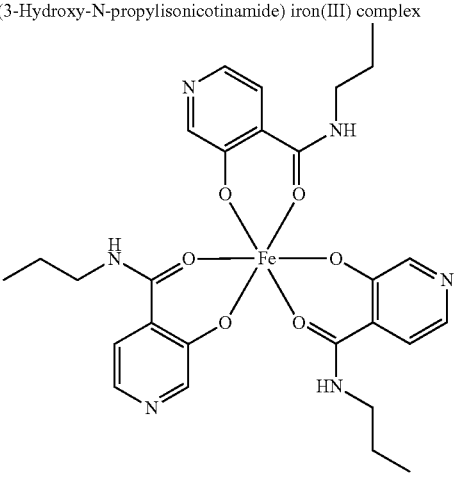

15 mmol (2.78 g) 3-hydroxy-N-propylisonicotinamide were provided in 70 ml ethanol and 15 mmol sodium methanolate (3.43 ml 25% solution in methanol) were added. 5 mmol (0.84 g) FeCl$_3$ (anhydrous) dissolved in 10 ml ethanol were added dropwise and stirred for 2 h. The reaction mixture was filtered, the filtrate was evaporated at a rotary evaporator and the residue was dried at 50° C. in a vacuum drying oven. 2.95 g (99% Fe-yield) of the title compound were obtained.

IR (in substance, cm$^{-1}$): 1582, 1549, 1473, 1437, 1403, 1323, 1270, 1246, 1216, 1145, 1125, 1069, 871, 825, 786, 699, 666.

CHN-elementary analysis: C, 50.87; H, 5.68; N, 13.10.
Fe-content: 9.41% [m/m]
chloride-content: 2.5% [m/m]

6. Tris-(N-Butyl-3-hydroxyisonicotinamide) iron(III) complex

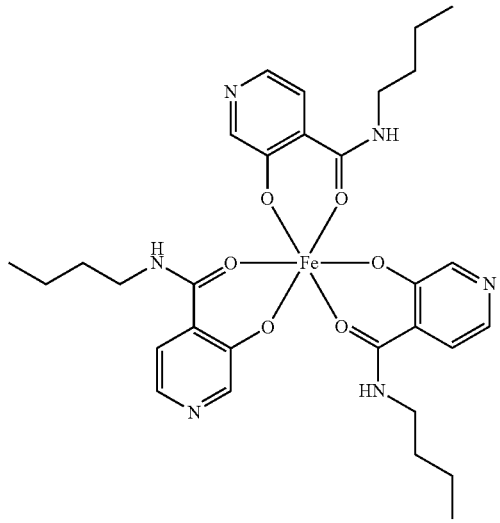

15 mmol (2.9 g) N-butyl-3-hydroxyisonicotinamide were provided in 50 ml ethanol and 5 mmol (0.81 g) FeCl$_3$ (anhydrous) dissolved in 5 ml ethanol were added as well as 30 mmol sodium hydrogen carbonate. It was stirred for 3 h, then the reaction mixture was filtered, the filtrate was evaporated at a rotary evaporator and the residue was dried at 50° C. in a vacuum drying oven. 3.1 g (92% Fe-yield) of the title compound were obtained.

IR (in substance, cm$^{-1}$): 1581, 1548, 1472, 1436, 1403, 1323, 1215, 1125, 1069, 979, 950, 836, 785, 740, 698, 666, 622, 590, 553, 526, 507.

CHN-elementary analysis: C, 54.80; H, 6.03; N, 12.70.
Fe-content: 8.32% [m/m]
chloride-content: 1.2% [m/m]

7. Tris-(3-Hydroxy-N-(2-methoxyethyl)isonicotinamide) iron(III) complex

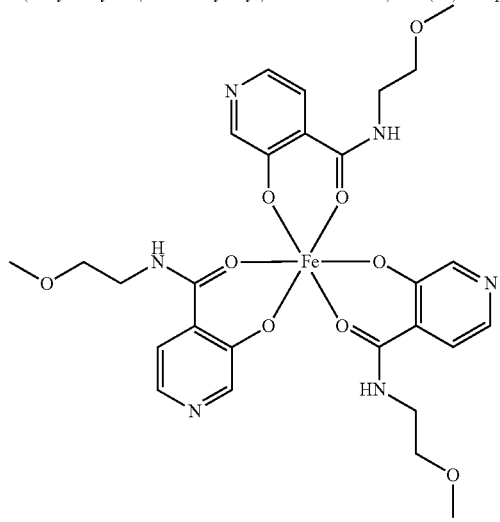

15.8 mmol (3.1 g) 3-hydroxy-N-(2-methoxyethyl)isonicotinamide were provided in 50 ml ethanol and 15 mmol (0.81 g) sodium methanolate dissolved in 5 ml methanol were added. 5.24 mmol (0.85 g) FeCl$_3$ (anhydrous) dissolved in 10 ml ethanol were added dropwise and stirred for 2 h. The reaction mixture was filtered, the filtrate was evaporated at a rotary evaporator and the residue dried at 50° C. in a vacuum drying oven. 3.1 g (85% Fe-yield) of the title compound were obtained.

IR (in substance, cm$^{-1}$): 1585, 1550, 1475, 1404, 1363, 1323, 1218, 1196, 1117, 1018, 962, 893, 826, 784, 671.

CHN-elementary analysis: C, 46.77; H, 5.38; N, 11.98.

Fe-content: 8.14% [m/m]

chloride-content: 3.2% [m/m]

8. Tris-(3-Hydroxy-N-(2-methoxyethyl)-N-methylisonicotinamide) iron(III) complex

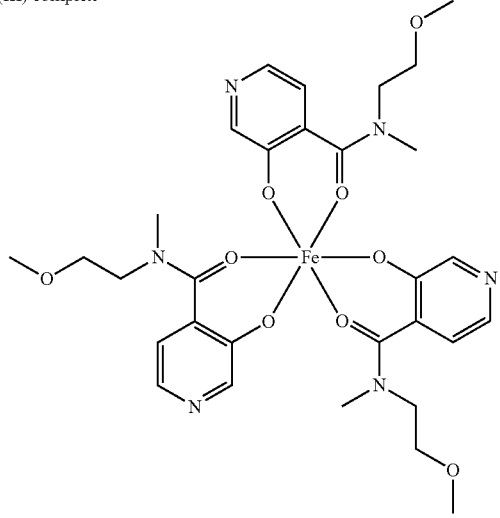

15 mmol (3.25 g) 3-hydroxy-N-(2-methoxyethyl)-N-methylisonicotinamide were provided in 50 ml ethanol and 15 mmol sodium methanolate (25% solution in methanol) were added. 5 mmol (0.84 g) FeCl$_3$ (anhydrous) dissolved in 10 ml ethanol were added dropwise and stirred for 2 h. The reaction mixture was filtered, the filtrate evaporated at a rotary evaporator and the residue dried at 50° C. in a vacuum drying oven. 3.4 g (98% Fe-yield) of the title compound were obtained.

IR (in substance, cm$^{-1}$): 1563, 1523, 1472, 1396, 1309, 1230, 1204, 1157, 1113, 1063, 1015, 976, 910, 823, 790, 729, 707, 650, 614.

CHN-elementary analysis: C, 50.32; H, 5.97; N, 11.60.

Fe-content: 8.18% [m/m]

chloride-content: 1.3% [m/m]

9. Tris-(3-Hydroxy-N,N-bis(2-methoxyethyl)isonicotinamide) iron(III) complex

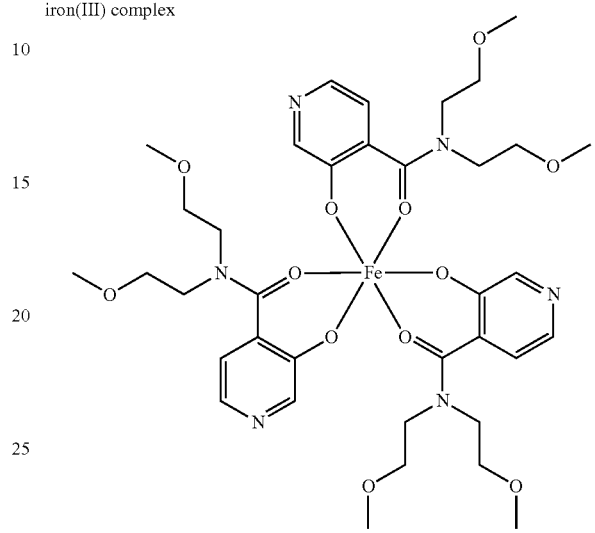

5.1 mmol (1.30 g) 3-hydroxy-N,N-bis(2-methoxyethyl)isonicotinamide were provided in 50 ml ethanol and 5.1 mmol sodium methanolate (1.17 ml 25% solution in methanol) were added. 1.7 mmol (0.277 g) FeCl$_3$ (anhydrous) dissolved in 10 ml ethanol were added dropwise and stirred for 2 h. The reaction mixture was filtered, the filtrate evaporated at a rotary evaporator and the residue dried at 50° C. in a vacuum drying oven. 1.53 g (98% Fe-yield) of the title compound were obtained.

IR (in substance, cm$^{-1}$): 1631, 1556, 1469, 1429, 1397, 1364, 1309, 1221, 1203, 1181, 1140, 1111, 1067, 1015, 824, 791, 726, 701.

CHN-elementary analysis: C, 50.17; H, 6.30; N, 9.72.

Fe-content: 6.06% [m/m]

chloride-content: 0.76% [m/m]

10. Tris(N,N-Diethyl-3-hydroxyisonicotinamide) iron(III) complex

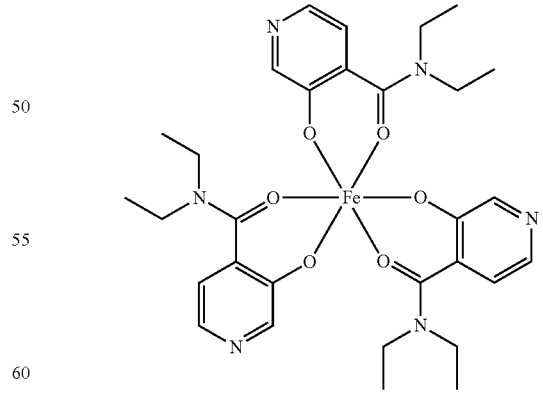

15 mmol (3.0 g) N,N-diethyl-3-hydroxyisonicotinamide were dissolved in 100 ml ethanol and 15 mmol sodium methanolate (25% solution in methanol) were added. 5 mmol (0.83 g) FeCl$_3$ (anhydrous) dissolved in 10 ml ethanol were added dropwise and stirred for 2 h. The reaction mixture was filtered, the filtrate evaporated at a rotary evaporator and the residue dried at 50° C. in a vacuum drying oven. 3.2 g (100% Fe-yield) of the title compound were obtained.

IR (in substance, cm$^{-1}$): 1557, 1520, 1471, 1397, 1362, 1308, 1259, 1222, 1159, 1095, 1062, 1004, 947, 893, 824, 789, 725, 697, 645, 610.

CHN-elementary analysis: C, 53.48; H, 6.25; N, 12.33.
Fe-content: 8.72% [m/m]
chloride-content: 1.1% [m/m]

11. Tris-((3-Hydroxypyridine-4-yl)(morpholino)methanone) iron(III) complex

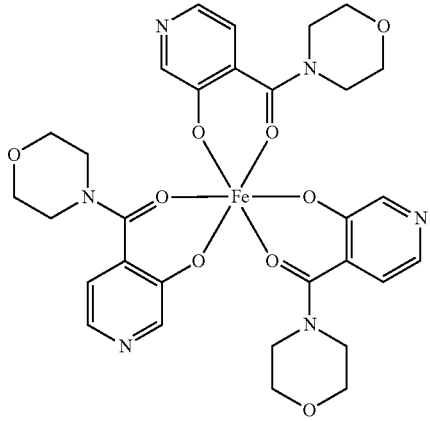

9 mmol (1.93 g) (3-hydroxypyridine-4-yl)(morpholino) methanone were provided in 50 ml ethanol and 9 mmol sodium methanolate (25% solution in methanol) were added. 3 mmol (0.497 g) FeCl$_3$ (anhydrous) dissolved in 10 ml ethanol were added dropwise and stirred for 2 h. The reaction mixture was filtered, the filtrate evaporated at a rotary evaporator and the residue dried at 50° C. in a vacuum drying oven. 2.2 g (98% Fe-yield) of the title compound were obtained.

IR (in substance, cm$^{-1}$): 1624, 1559, 1523, 1469, 1435, 1398, 1361, 1305, 1281, 1266, 1219, 1181, 1137, 1110, 1063, 1022, 939, 902, 865, 827, 788, 724, 705, 626.

CHN-elementary analysis: C, 50.36; H, 5.52; N, 11.48.
Fe-content: 7.43% [m/m]
chloride-content: 0.67% [m/m]

12. Tris-((3-Hydroxypyridine-4-yl)(piperidine-1-yl)methanone iron(III) complex

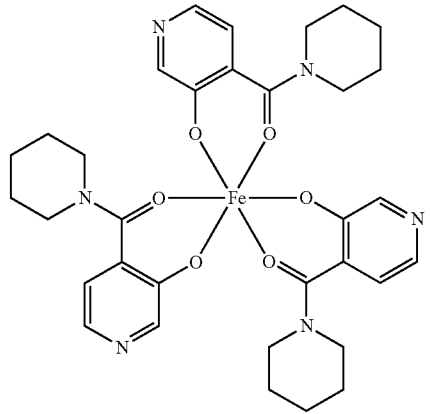

15 mmol (3.12 g) (3-hydroxypyridine-4-yl)(piperidine-1-yl) methanone were provided in 80 ml ethanol and 15 mmol sodium methanolate (25% solution in methanol) were added. 5 mmol (0.83 g) FeCl$_3$ (anhydrous) dissolved in 10 ml ethanol were added dropwise and stirred for 2 h. The reaction mixture was filtered, the filtrate evaporated at a rotary evaporator and the residue dried at 50° C. in a vacuum drying oven. 3.3 g (98% Fe-yield) of the title compound were obtained.

IR (in substance, cm$^{-1}$): 1556, 1524, 1469, 1442, 1397, 1309, 1285, 1258, 1235, 1216, 1187, 1149, 1105, 1062, 1025, 1004, 954, 927, 894, 853, 822, 788, 724, 701, 646, 616.

CHN-elementary analysis: C, 55.39; H, 6.024; N, 11.48.
Fe-content: 8.27% [m/m]
chloride-content: 0.88% [m/m]

13. Tris-((3-Hydroxypyridine-4-yl)(pyrrolidine-1-yl)methanone) iron(III) complex

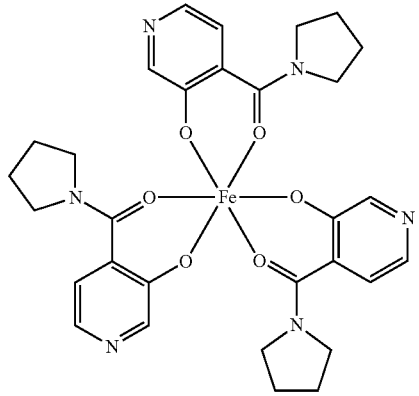

9 mmol (1.73 g) (3-hydroxypyridine-4-yl)(pyrrolidine-1-yl) methanone were provided in 70 ml ethanol and 9 mmol sodium methanolate (2.06 ml 25% solution in methanol) were added. 3 mmol (0.497 g) FeCl$_3$ (anhydrous) dissolved in 10 ml ethanol were added dropwise and stirred for 2 h. The reaction mixture was filtered, the filtrate evaporated at a rotary evaporator and the residue dried at 50° C. in a vacuum drying oven. 1.98 g (94% Fe-yield) of the title compound were obtained.

IR (in substance, cm$^{-1}$): 1552, 1517, 1452, 1393, 1310, 1272, 1223, 1205, 1171, 1128, 1065, 914, 871, 827, 787, 741, 712, 657.

CHN-elementary analysis: C, 53.47; H, 5.49; N, 12.26.
Fe-content: 7.98% [m/m]
chloride-content: 1.85% [m/m]

Testing Method:

The excellent Fe utilizations that can be accomplished through the Fe complexes according to the invention were measured by means of the following mouse model.

Male NMRI (SPF) mice (approximately 3 weeks old) were fed a low-iron diet (approx. 5 ppm iron) for approximately 3 weeks. The iron complexes were then administered to them by means of a stomach tube (2 mg iron/kg body weight/day) for 2 times 5 days, with an interruption of 2 days (days 1-5 and 8-12). 6 mice were the control group (negative control) and were administered with water instead. Utilization on day 15 was calculated from the hemoglobin increase and the body weight increase in accordance with the formula $$\text{Utilisation (\%)} = \frac{\Delta \text{Eisenutilisation} * 100}{Fe Dos.} = \frac{(Fe\ ut. - Fe\ ut.\ \text{Control}) * 100}{Fe Dos.}$$

$$= [(Hb_{2(3)} * BW_{9(14)} - Hb_1 * BW_4) * 0{,}07 * 0{,}0034 - (HB_{2(3)Control} *$$
$$BW_{9(14)Control} - Hb_{1Control} * BW_{4Control}) * 0{,}07 * 0{,}0034)] * 100 / Fe\ Dos.$$

$$= [(Hb_{2(3)} * BW_{9(14)} - Hb_1 * BW_4) * 0{,}000238 - (Hb_{2(3)Control} *$$
$$BW_{9(14)Control} - Hb_{1Control} * BW_{4Control}) * 0{,}000238] * 100 / Fe\ Dos.$$

$$= (Hb_{2(3)} * BW_{9(14)} - Hb_1 * BW_4 - Hb_{2(3)Control} * BW_{9(14)Control} +$$
$$Hb_{1Control} * BW_{4Control}) * 0{,}0238 / Fe\ Dos.$$

0.07=Factor for 70 ml blood per kg body weight (BW)
0.0034=Factor for 0.0034 g Fe/g Hb
$Hb_1$=Hemoglobin level (g/l) on day 1

$Hb_{2(3)}$=Hemoglobin level (g/l) on day 8 (or 15)
$BW_4$=body weight (g) on day 1
$BW_{9(14)}$=body weight (g) on day 8 (or 15)
$Hb_{1\ Control}$=average hemoglobin level (g/l) on day 1 in the control group,
$Hb_{2(3)\ Control}$=average hemoglobin level (g/l) on day 8 (or 15) in the control group,
$BW_{4\ Control}$=average body weight (g) on day 1 in the control group,
$BW_{9(14)\ Control}$=average body weight (g) on day 8 (or 15) in the control group,
Fe Dos.=entire administered iron (mg Fe) over 5 or 10 days,
Fe ut.=$(Hb_{2(3)}*BW_{9(14)}-Hb_1*BW_4)*0.07*0.0034$ (mg Fe)
Δ Utilization=Fe tot. utilized (examined group)–Fe ut. Control group, utilized from food, (mg Fe)

The following table 1 shows the iron utilization:

TABLE 1

| Example No. | Utilization n 15 d (abs. %) | Standard deviation (+/−0,5) |
|---|---|---|
| 1 | 68 | 11 |
| 6 | 76 | 10 |
| 7 | 76 | 10 |

COMPARATIVE EXAMPLES

As comparative examples the ligands as described in WO2011117225

AAO. N,N-dimethyl-2-oxocyclohexane carboxamide

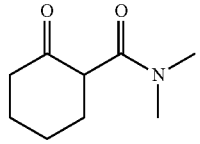

and

AAP. N,N-dimethyl-2-oxocyclopentane carboxamide

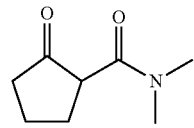

as well as the complex compound according to Example 66

Tris-(N,N-dimethyl-2-oxocyclopentane carboxamide) iron(III) complex

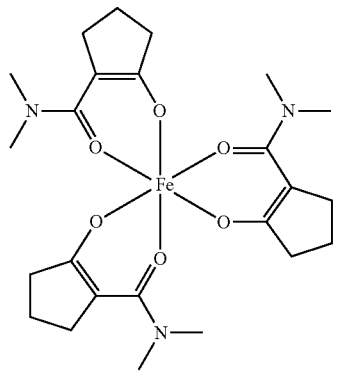

have been prepared.

The complex according to Example 66 of WO 2011117225 shows only very low stability. Although it was possible to obtain the iron complex and to carry out the in vitro test, it was not possible, due to its low stability, to find a formulation, which allowed the further in vivo testing with the aforementioned mice model.

The ligand with the analog 6-membered ring structure (ligand AAO) was even less stable. Here it was possible to prepare the ligand, however, the complex was so unstable that purification and analytical measurement thereof was not possible, let alone its in vitro or in vivo testing.

Due to its very low stability such compounds must be considered as totally unsuitable for medical applications.

It was surprisingly possible to solve the aforementioned problems with the new complexes of the present invention. It was possible to show in the in vivo testing that these complexes exhibit sufficient stability and can be well used in a medical application in the iron therapy. The mouse model testing provided excellent utilization data.

The measured iron utilization values are an important parameter with respect to the indication of the treatment of iron deficiency symptoms and iron deficiency anemia, because this parameter does not only reflect the iron adsorption but also the relation between body weight and iron adsorption, which is particularly important when using adolescent animals in the animal model. If only the hemoglobin levels were examined, which are a measure for the effectively adsorbed iron, the amount which is based on the growth of the animals would remain unconsidered. Accordingly, the iron utilization is a more concrete measure, although iron utilization and hemoglobin level mostly correlate with each other. An examination solely of the iron serum level, which can be measured, too, is to be less considered as therewith a prediction about the amount of iron can be given, which reaches the body, but not about the amount thereof which can be used by the body.

The test results show, that the iron complex compounds of the present invention exhibit excellent iron utilization, which makes the suitable as an agent for the treatment of iron deficiency anemia and the symptoms associated therewith.

PREFERRED EMBODIMENTS

Further preferred embodiments according to the present invention:
1. Iron(III)-3-hydroxyisonicotinamide complex compounds or pharmaceutically acceptable salts thereof for the use in the treatment and prophylaxis of iron deficiency symptoms and iron deficiency anemias.
2. Iron(III) complex compounds for the use according to embodiment 1, containing at least one ligand of the formula (I):

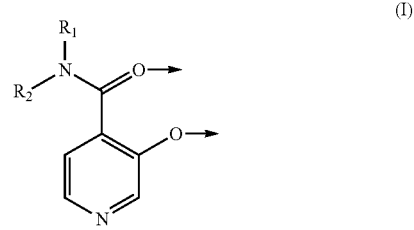

(I)

wherein
the arrows respectively represent a coordinate bond to one or different iron atoms;
$R_1$ and $R_2$ are the same or different and are each selected from the group consisting of:

hydrogen and
optionally substituted alkyl, or wherein
$R_1$ and $R_2$ together with the nitrogen atom to which they are bonded form an optionally substituted 3- to 6-membered ring, which may optionally contain a further heteroatom;
or pharmaceutically acceptable salts thereof.

3. Iron(III) complex compounds for the use according to embodiment 1 or 2, containing at least one ligand of the formula (I):

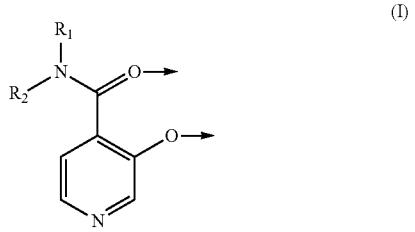

(I)

wherein
the arrows respectively represent a coordinate bond to one or different iron atoms,
$R_1$ and $R_2$ are the same or different and are each selected from the group consisting of:
hydrogen, and
optionally substituted alkyl,
or pharmaceutically acceptable salts thereof.

4. Iron(III) complex compounds for the use according to any of the embodiments 1 to 3, containing at least one ligand of the formula (I):

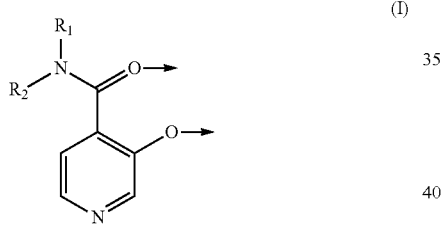

(I)

wherein
the arrows respectively represent a coordinate bond to one or different iron atoms,
$R_1$ and $R_2$ are the same or different and are each selected from the group consisting of:
hydrogen, and
alkyl, which may be substituted with an alkoxy or a hydroxy group, preferably with an alkoxy group, also comprising alkyl, wherein one or two methylene groups (—$CH_2$—) may be replaced by —O—,
or pharmaceutically acceptable salts thereof.

5. Iron(III) complex compounds for the use according to any of the embodiments 1 to 4, containing at least one ligand of the formula (I):

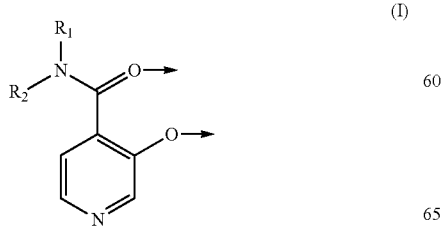

(I)

wherein
the arrows respectively represent a coordinate bond to one or different iron atoms,
$R_1$ and $R_2$ are the same or different and are each selected from the group consisting of: hydrogen, methyl, ethyl, propyl, isopropyl, n-butyl, sek-butyl isobutyl, methoxyethyl, ethoxyethyl, methoxypropyl and ethoxypropyl, methoxyethoxyethyl, ethoxyethoxyethyl, propoxyethoxyethyl; or pharmaceutically acceptable salts thereof.

6. Iron(III) complex compounds for the use according to any of the embodiments 1 to 5, containing at least one ligand of the formula (I):

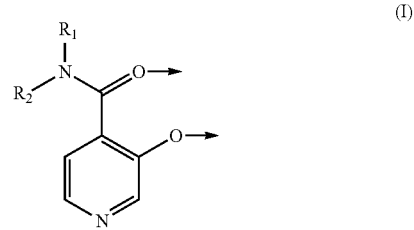

(I)

wherein
the arrows respectively represent a coordinate bond to one or different iron atoms,
$R_1$ and $R_2$ are the same of different and are each selected from the group consisting of optionally substituted alkyl, preferably of methyl and ethyl, or pharmaceutically acceptable salts thereof.

7. Iron(III) complex compounds for the use according to any of the embodiments 1 to 6 of the formula (II):

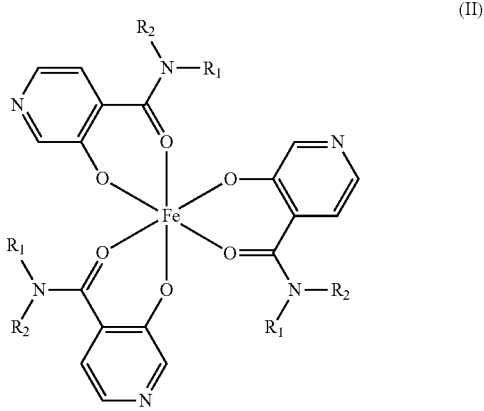

(II)

wherein $R_1$ and $R_2$ are as defined above
or pharmaceutically acceptable salts thereof.

8. Iron(III) complex compounds for the use according to any of the embodiments 1 to 7 for the treatment and prophylaxis of prophylaxis of iron deficiency symptoms and iron deficiency anemias and the symptoms associated therewith.

9. Iron(III) complex compounds for the use according to embodiment 8, wherein the symptoms include: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections, depressive moods.

10. Iron(III) complex compounds for the use according to any of the embodiments 1 to 9 for the treatment of iron deficiency anemia in pregnant women, latent iron deficiency anemia in children and adolescents, iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to psilosis (sprue), iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CKD 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD).

11. Iron(III) complex compounds for the use according to any of the embodiments 1 to 10 for oral administration.
12. Iron(III) complex compounds according to embodiment 11 for administration in the form of a tablet or a capsule.
13. Medicament containing iron(III) complex compounds as defined in any of the embodiments 1 to 7.
14. Medicament containing iron(III) complex compounds as defined in any of the embodiments 1 to 7 and at least one physiological compatible carrier or excipient.
15. Composition containing iron(III) complex compounds as defined in any one of embodiments 1 to 7, in combination with at least one further medicament which acts on the iron metabolism.

The invention claimed is:

1. A method of treatment and/or prophylaxis of iron deficiency symptoms and/or iron deficiency anemias in a human or animal, comprising administering to the human or animal at least one iron(III)-3-hydroxyisonicotinamide complex, or at least one pharmaceutically acceptable salt thereof.

2. The method of claim 1, wherein the at least one iron(III)-3-hydroxyisonicotinamide complex compound comprise at least one ligand of the formula (I):

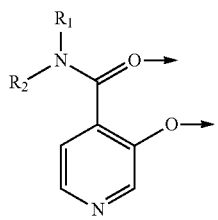

wherein
the arrows respectively represent a coordinate bond to one or different iron atoms;
$R_1$ and $R_2$ are the same or different and are each selected from the group consisting of:
hydrogen and
optionally substituted alkyl, or wherein
$R_1$ and $R_2$ together with the nitrogen atom to which they are bonded form an optionally substituted 3- to 6-membered ring, which may optionally contain a further heteroatom;
or pharmaceutically acceptable salts thereof.

3. The method of claim 1, wherein the at least one iron(III)-3-hydroxyisonicotinamide complex compound comprises at least one ligand of the formula (I):

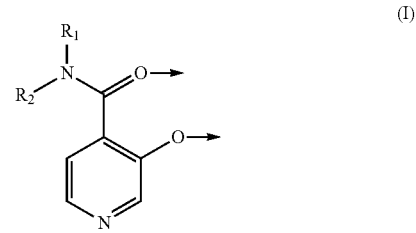

wherein
the arrows respectively represent a coordinate bond to one or different iron atoms, $R_1$ and $R_2$ are the same or different and are each selected from the group consisting of:
hydrogen, and
alkyl, which may be substituted with an alkoxy, also comprising alkyl, wherein one or two methylene groups (—$CH_2$—) may be replaced by —O—, or wherein
$R_1$ and $R_2$ together with the nitrogen atom to which they are bonded form an optionally substituted 5- to 6-membered ring, which may optionally contain a further heteroatom;
or pharmaceutically acceptable salts thereof.

4. The method of claim 3, wherein at least one of $R_1$ and $R_2$ is alkyl, which may be substituted with a hydroxy group.

5. The method of claim 1, wherein the at least one iron(III)-3-hydroxyisonicotinamide complex compound comprises at least one ligand of the formula (I):

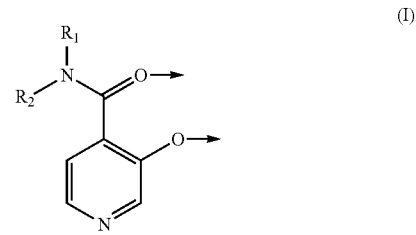

wherein
the arrows respectively represent a coordinate bond to one or different iron atoms, $R_1$ and $R_2$ are the same or different and are each selected from the group consisting of: hydrogen, methyl, ethyl, propyl, isopropyl, n-butyl, sec-butyl isobutyl, methoxyethyl, ethoxyethyl, methoxypropyl and ethoxypropyl, methoxyethoxyethyl, ethoxyethoxyethyl, propoxyethoxyethyl; or wherein
$R_1$ and $R_2$ together with the nitrogen atom to which they are bonded form an optionally substituted 5- to 6-membered ring, which is selected from the group consisting of morpholinyl, piperidinyl and pyrrolidinyl;
or pharmaceutically acceptable salts thereof.

6. The method of claim 1, wherein the at least one iron(III)-3-hydroxyisonicotinamide complex compound comprises at least one ligand of the formula (I):

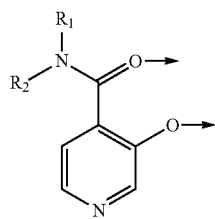
(I)

wherein
the arrows respectively represent a coordinate bond to one or different iron atoms, $R_1$ and $R_2$ are the same of different and are each selected from the group consisting of hydrogen, optionally substituted alkyl, selected from the group consisting of methyl, ethyl, propyl, n-butyl and alkyl which is substituted with a methoxy group or an ethoxy group; or wherein $R_1$ and $R_2$ together with the nitrogen atom to which they are bonded form a heterocyclic 5- to 6-membered ring, which is selected from the group consisting of morpholinyl, piperidinyl and pyrrolidinyl;

or pharmaceutically acceptable salts thereof.

7. The method of claim 1, wherein at least one iron(III)-3-hydroxyisonicotinamide complex compound has the formula (II):

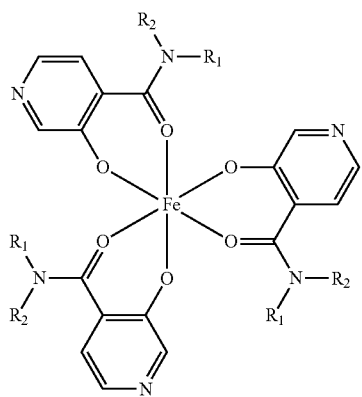
(II)

or pharmaceutically acceptable salts thereof.

8. The method of claim 1, wherein the at least one iron(III)-3-hydroxyisonicotinamide complex compound comprises are selected from the group consisting of:

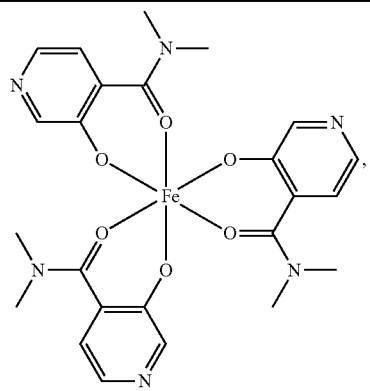

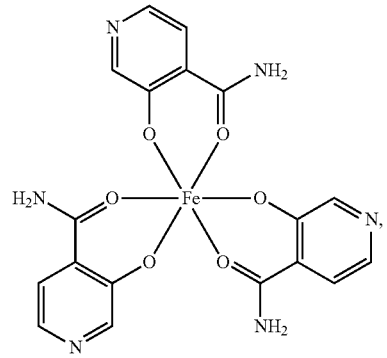

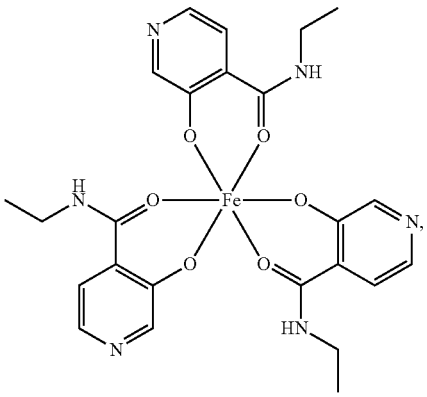

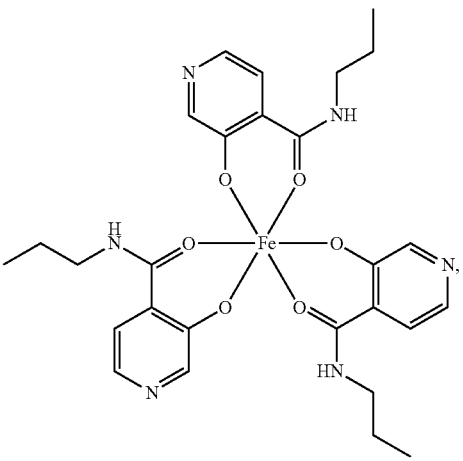

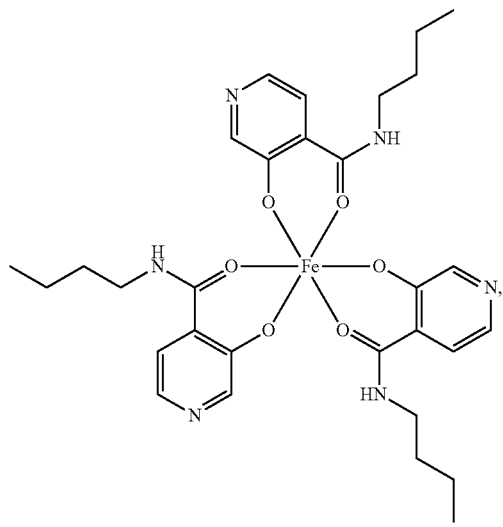
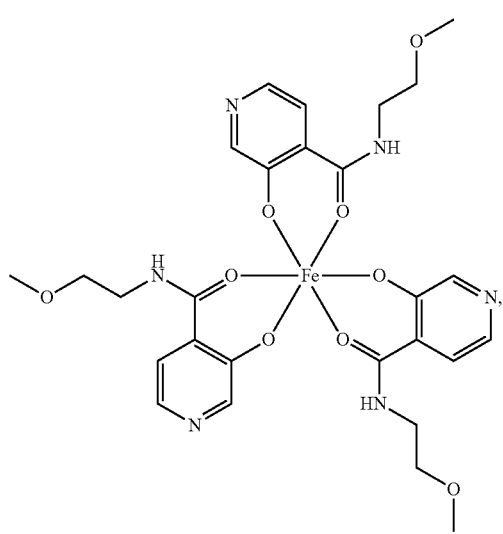
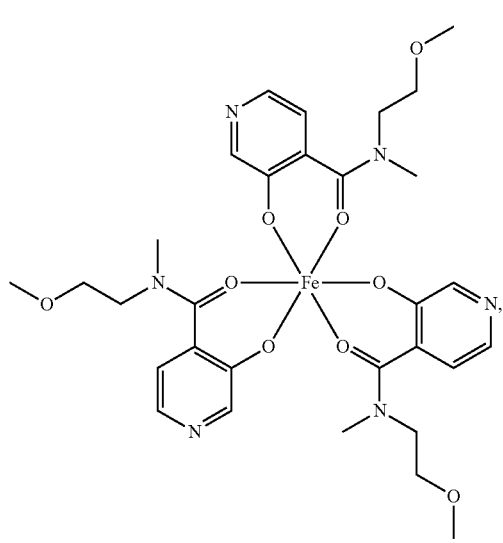
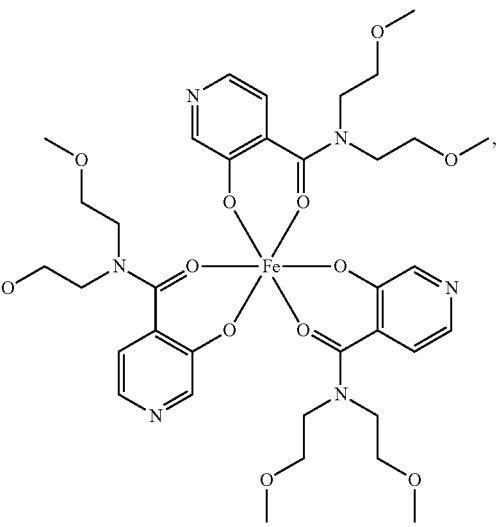
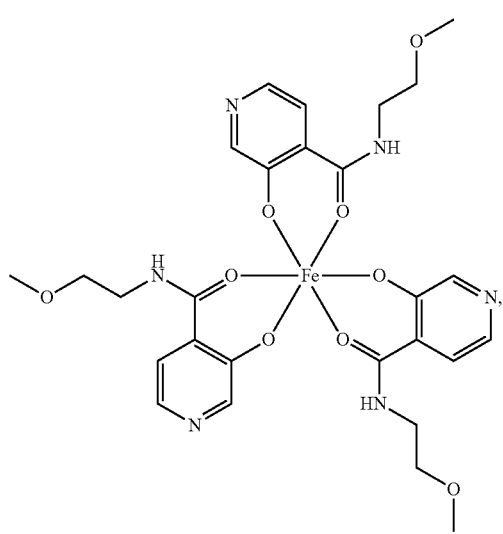
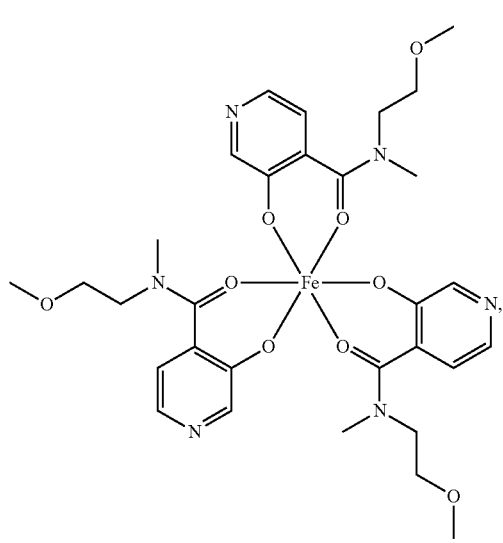

-continued

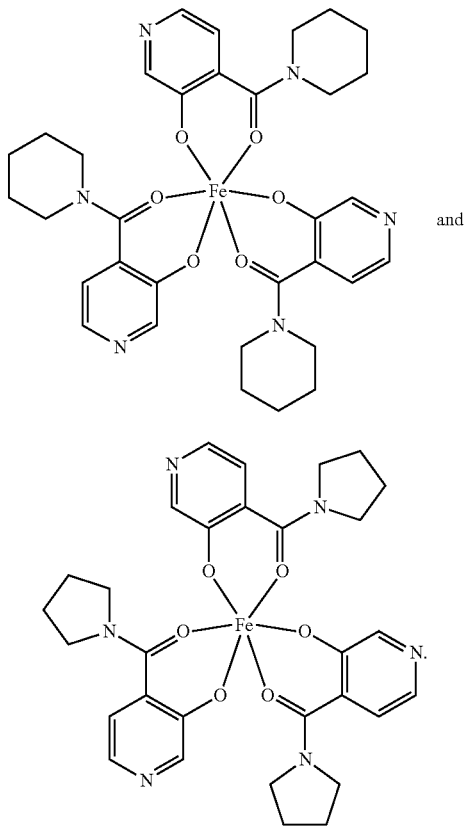

and

9. The method of claim 1, wherein the iron(III) complex compounds are contained in a medicament.

10. The method of claim 1, wherein the treatment and/or prophylaxis is for iron deficiency symptoms, wherein the iron deficiency symptoms are selected from the group consisting of: fatigue, listlessness, lack of concentration, low cognitive efficiency, difficulties in finding the right words, forgetfulness, unnatural pallor, irritability, acceleration of heart rate (tachycardia), sore or swollen tongue, enlarged spleen, desire for strange foods (pica), headaches, lack of appetite, increased susceptibility to infections, depressive moods, and combinations thereof.

11. The method of claim 1, wherein the iron deficiency symptoms and/or iron deficiency anemias are selected from the group consisting of iron deficiency anemia in pregnant women, latent iron deficiency anemia in children and adolescents, iron deficiency and iron deficiency anemia in children suffering from attention-deficit/hyperactivity disorder (ADHD), iron deficiency anemia caused by gastrointestinal abnormalities, iron deficiency anemia due to blood loss, such as gastrointestinal hemorrhage (e.g. due to ulcers, carcinoma, hemorrhoids, inflammatory disorders, taking of acetylsalicylic acid), iron deficiency anemia caused by menstruation, iron deficiency anemia caused by injuries, iron deficiency anemia due to psilosis (sprue), iron deficiency anemia due to reduced dietary iron uptake, in particular in selectively eating children and adolescents, immunodeficiency caused by iron deficiency anemia, brain function impairment caused by iron deficiency anemias, restless leg syndrome caused by iron deficiency anemias, iron deficiency anemias in the case of cancer, iron deficiency anemias caused by chemotherapies, iron deficiency anemias triggered by inflammation (AI), iron deficiency anemias in the case of congestive cardiac insufficiency (CHF; congestive heart failure), iron deficiency anemias in the case of chronic renal insufficiency stage 3-5 (CKD 3-5; chronic kidney diseases stage 3-5), iron deficiency anemias triggered by chronic inflammation (ACD), iron deficiency anemias in the case of rheumatoid arthritis (RA), iron deficiency anemias in the case of systemic lupus erythematosus (SLE) and iron deficiency anemias in the case of inflammatory bowel diseases (IBD).

12. The method of claim 1, wherein the iron(III) complex compounds are orally administered.

13. The method of claim 1, wherein the iron(III) complex compounds are administered in the form of a tablet or a capsule.

14. The method of claim 13, wherein the tablet or capsule further comprises at least one physiologically compatible carrier or excipient.

15. The method of claim 9, wherein the method further comprises administering at least one additional medicament which acts on the iron metabolism.

* * * * *